United States Patent
Gullotti et al.

(10) Patent No.: US 12,232,823 B2
(45) Date of Patent: Feb. 25, 2025

(54) INTRAOPERATIVE ALIGNMENT ASSESSMENT SYSTEM AND METHOD

(71) Applicant: GLOBUS MEDICAL, INC., Audubon, PA (US)

(72) Inventors: David Michael Gullotti, Towson, MD (US); Amir Hossein Soltanianzadeh, Baltimore, MD (US); Nicholas Theodore, Ruxton, MD (US); Edward Frederick Ruppel, III, Saratoga, MD (US); Saki Fujita, Baltimore, MD (US); Nicholas Griesmer Franconi, Pittsburgh, PA (US); Miguel Antonio Inserni, Alamo, CA (US); Jennifer Lin, Oceanside, NY (US); Robert Li, Cypress, CA (US); Ali Uneri, Baltimore, MD (US); Sritam Parashar Rout, Dracut, MA (US); Marc Chelala, Montreal (CA); Kyle Robert Cowdrick, Lilburn, GA (US); Maria Fernanda Torres, Caracas (VE)

(73) Assignee: Globus Medical, Inc., Audubon, PA (US)

( * ) Notice: Subject to any disclaimer, the term of this patent is extended or adjusted under 35 U.S.C. 154(b) by 110 days.

(21) Appl. No.: 17/663,845

(22) Filed: May 18, 2022

(65) Prior Publication Data
US 2022/0370146 A1  Nov. 24, 2022

Related U.S. Application Data

(60) Provisional application No. 63/190,750, filed on May 19, 2021.

(51) Int. Cl.
*A61B 34/20* (2016.01)
*A61B 6/50* (2024.01)

(52) U.S. Cl.
CPC .............. *A61B 34/20* (2016.02); *A61B 6/505* (2013.01); *A61B 2034/2055* (2016.02)

(58) Field of Classification Search
CPC ... A61B 34/20; A61B 6/50; A61B 2090/3983; A61B 2034/2055; A61B 6/505; A61B 2090/3966; A61B 90/39
See application file for complete search history.

(56) References Cited

U.S. PATENT DOCUMENTS

| | | | |
|---|---|---|---|
| 11,553,969 B1 * | 1/2023 | Lang | G06T 7/0012 |
| 11,608,666 B2 | 3/2023 | Bruck | |

(Continued)

FOREIGN PATENT DOCUMENTS

| | | |
|---|---|---|
| JP | 2015-502766 A | 2/2014 |
| JP | 2020-526364 A | 8/2020 |

(Continued)

*Primary Examiner* — Mark D Remaly

(57) ABSTRACT

Some embodiments provide systems, assemblies, and methods of analyzing patient anatomy, including providing an analysis of a patient's spine, and also analyzing the biomechanical effects of implants. In some embodiments, the systems, assemblies, and/or methods can include obtaining initial patient data, acquiring spinal alignment and contour information, acquiring flexibility and/or biomechanical information, registering patient anatomical landmarks of interest relative to fiducial markers, analyzing databases of measurements and patient data to predict postoperative patient outcomes. Further, in some embodiments, the systems, assemblies, and/or methods can assess localized anatomical features of the patient, and obtain anatomical region data. In some embodiments, the systems, assemblies, and/or methods can also analyze the localized anatomy and therapeutic device location and contouring. Further, the systems, assemblies, and/or methods can output localized anatomical analyses and therapeutic device contouring data and/or imagery on a display according to some embodiments.

11 Claims, 19 Drawing Sheets

(56) References Cited

U.S. PATENT DOCUMENTS

| | | | | |
|---|---|---|---|---|
| 2008/0004633 A1* | 1/2008 | Arata | ..................... | A61B 34/20 |
| | | | | 606/130 |
| 2015/0362596 A1 | 12/2015 | Nozaki | | |
| 2019/0000372 A1* | 1/2019 | Gullotti | .............. | A61B 17/7077 |
| 2020/0197100 A1* | 6/2020 | Leung | .................... | A61B 34/20 |

FOREIGN PATENT DOCUMENTS

| | | | | |
|---|---|---|---|---|
| WO | WO-2015054543 A1 * | 4/2015 | ......... | A61B 17/7002 |
| WO | WO-2018163105 A2 * | 9/2018 | ............. | A61B 34/20 |

\* cited by examiner

FIG. 1B
FIG. 1C
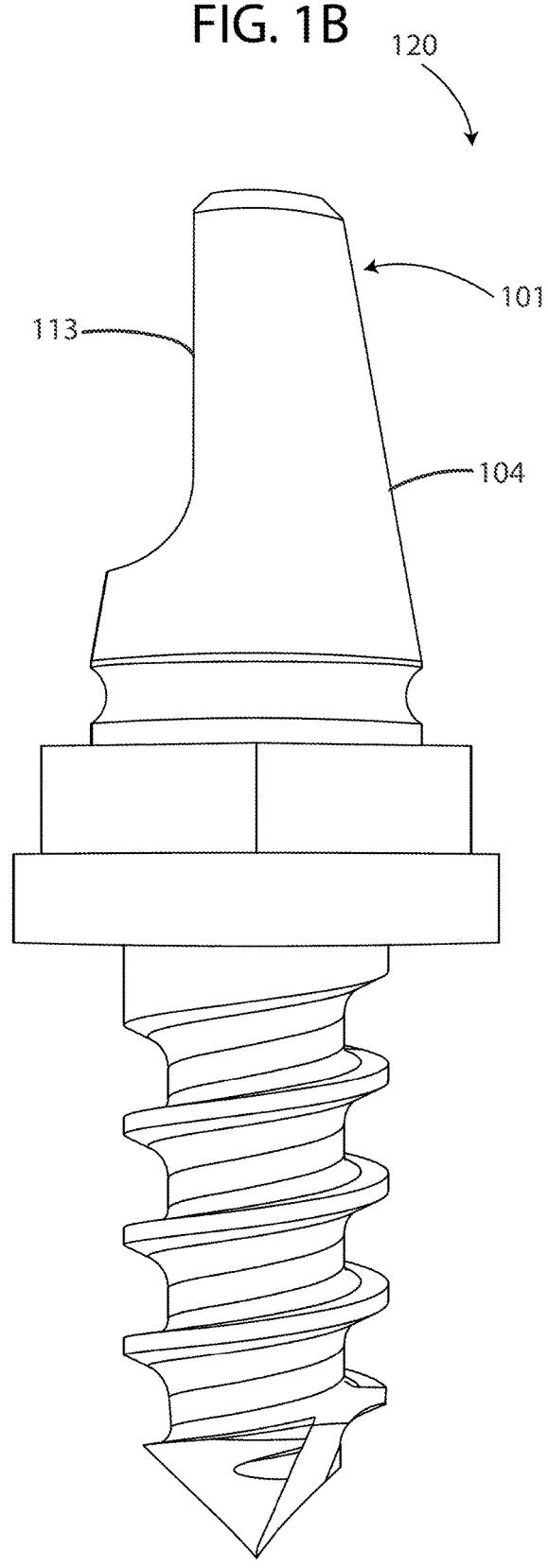
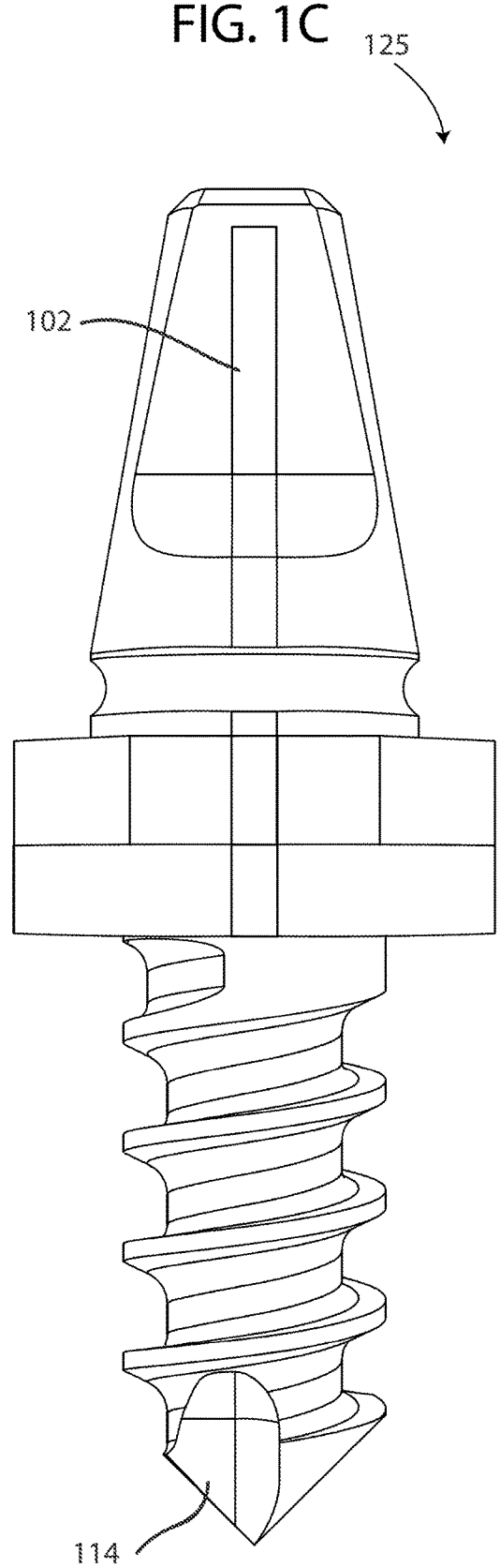

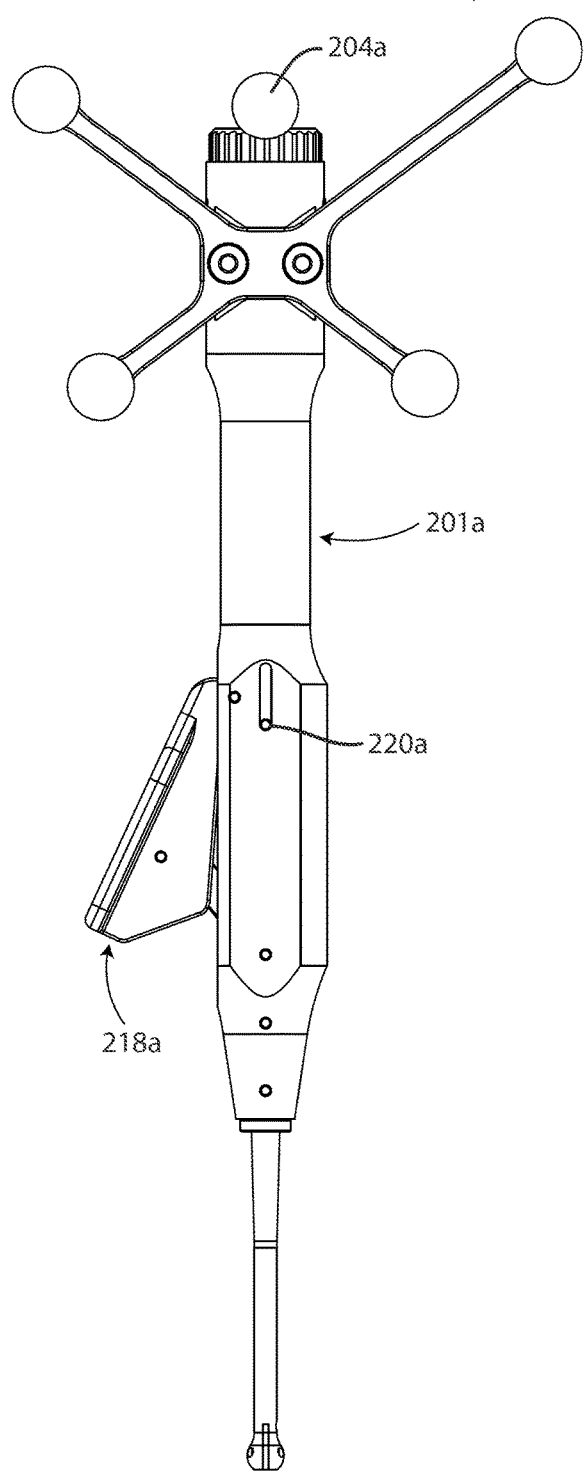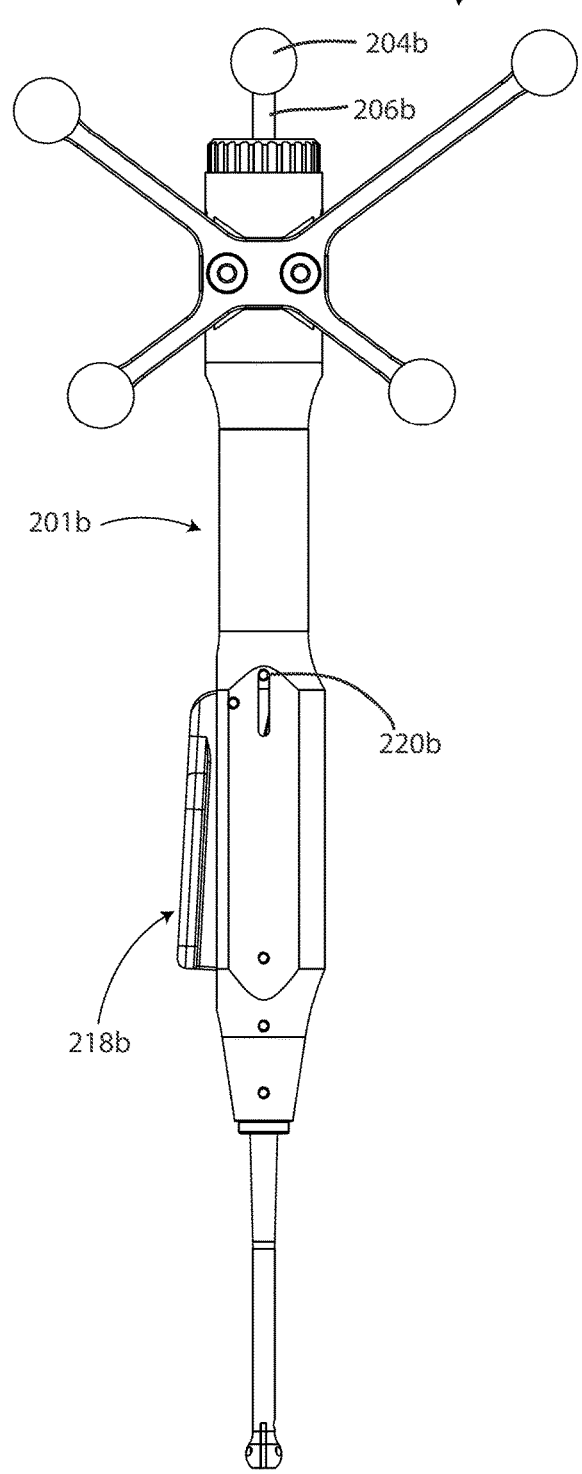

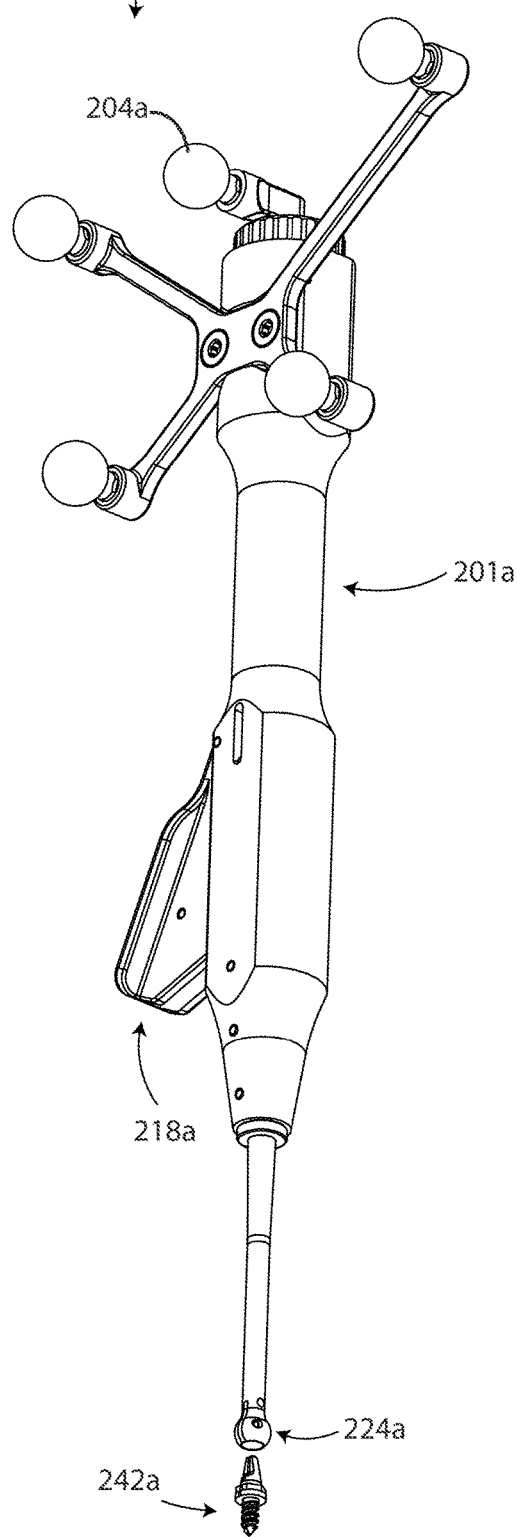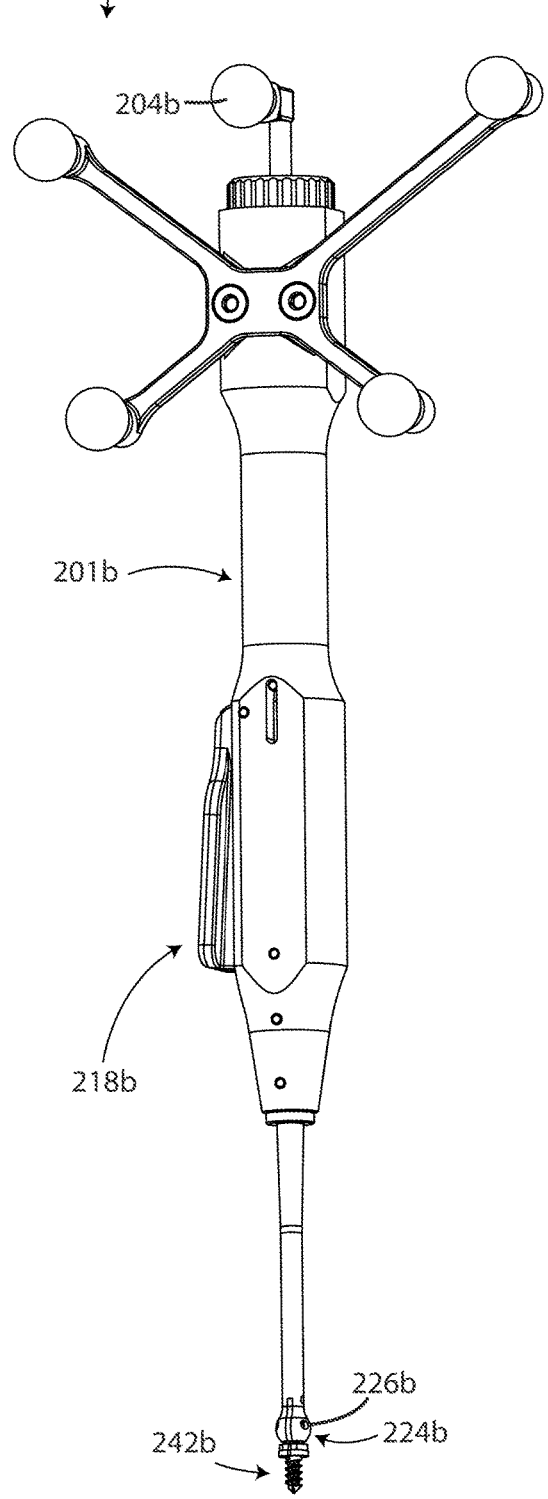

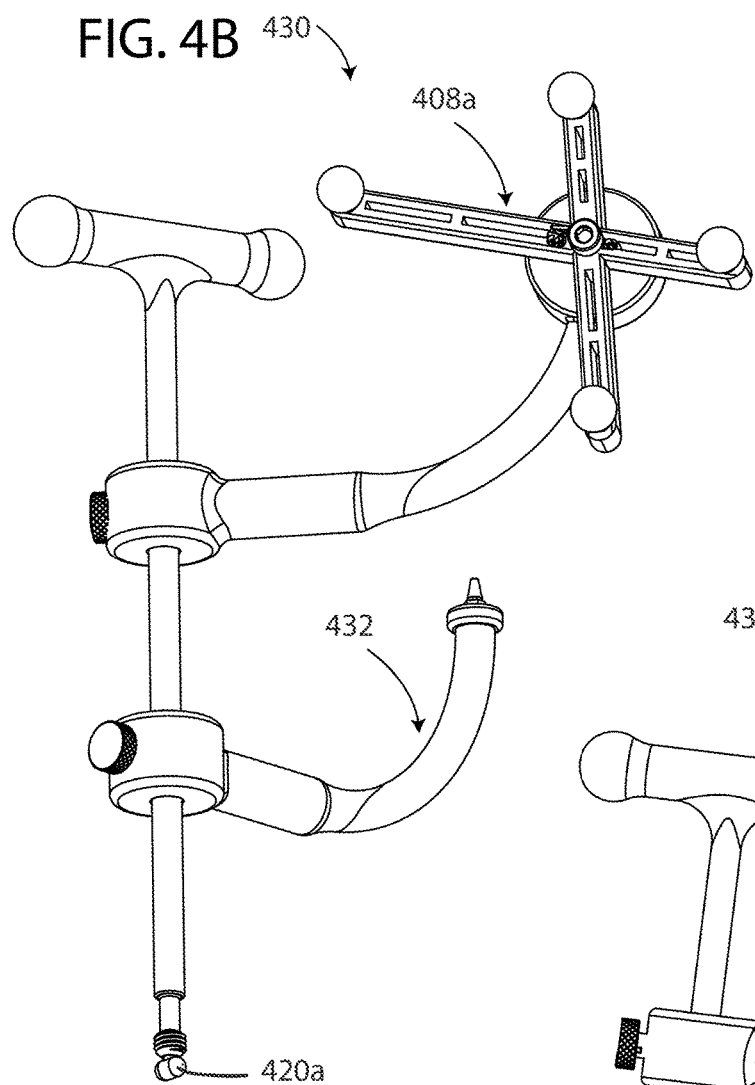
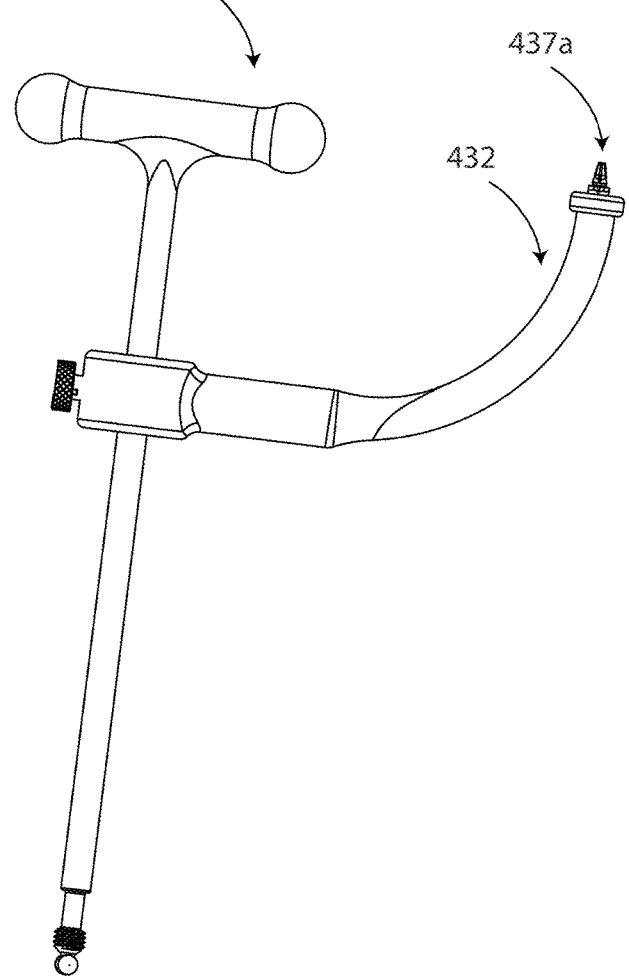

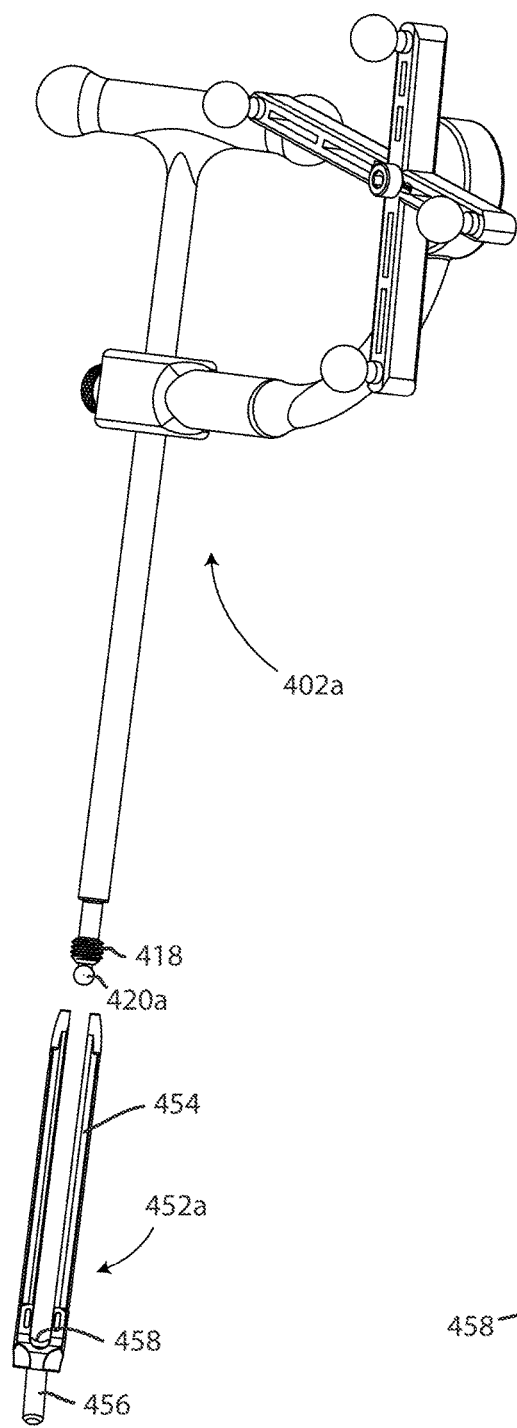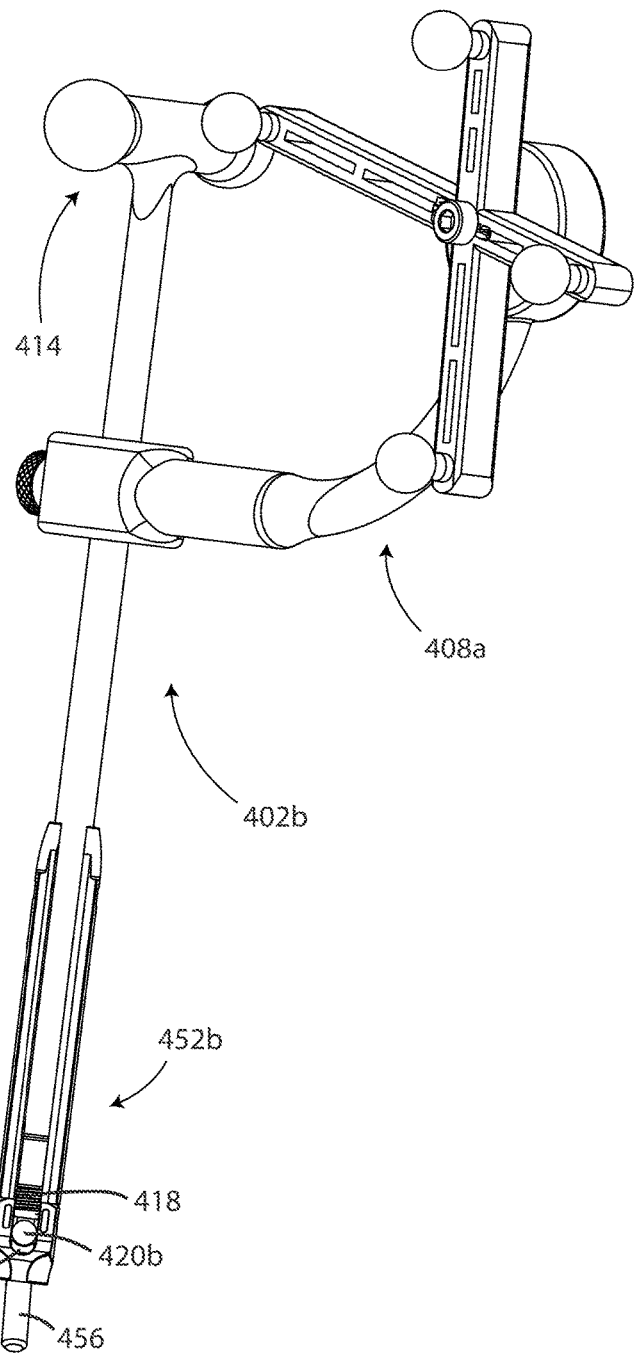

INTRAOPERATIVE ALIGNMENT ASSESSMENT SYSTEM AND METHOD

CROSS REFERENCE TO RELATED APPLICATIONS

This application is a non-provisional application claiming priority to provisional application Ser. No. 63/190,750 filed on May 19, 2022 which is incorporated in its entirety herein.

BACKGROUND

Current tools limit a surgeon's ability to quickly and accurately assess the intraoperative alignment of their patient's spine, especially after the spine has been manipulated during a correction. In addition, most of the state-of-the-art options introduce or rely on excessive radiation exposure, inadequate visualization of anatomical landmark(s) of interest, and lengthy disruptions to the surgical workflow.

Accordingly, new systems and methods are needed analyzing and providing a patient's spinal alignment information and therapeutic device data. The method ideally should include obtaining initial patient data, and acquiring spinal alignment contour information, assessing localized anatomical features of the patient, and obtaining anatomical region data. The system and method should include analyzing the localized anatomy and therapeutic device location and contouring resulting in an output including a localized anatomical analysis and a display of therapeutic device contouring data.

SUMMARY

Some embodiments include a system comprising at least one dynamic reference frame (DRF) configured so that any fixed or mobile portion of the DRF, or any assembly or component coupled to the DRF can be registered in 3D space using a plurality of trackable markers. In some embodiments, the plurality of trackable markers includes at least one moveable or triggerable marker. Some embodiments include at least one user-actuation trigger or actuator coupled to the at least one moveable or triggerable marker that can trigger or actuate the at least one moveable or triggerable marker. Some further embodiments include at least one 3D tracking camera or imaging system configured to track one or more of the plurality of trackable markers. In some embodiments, the system includes a processor and a memory coupled to the processor, wherein the memory stores instructions executable by the processor to track one or more 3D coordinates of one or more of the plurality of trackable markers.

Some further embodiments include a method of analyzing and providing spinal alignment anatomical information and therapeutic device data, comprising obtaining initial patient data, acquiring alignment contour information, assessing localized anatomical features, obtaining anatomical region data, analyzing localized anatomy, analyzing therapeutic device location and contouring, and/or outputting on a display the localized anatomical analyses and therapeutic device contouring data.

Some embodiments include radiopaque markers configured to be visually observable using an X-ray source or imager, where the radiopaque markers are at least partially embedded in the fiducial adapter assembly.

Some embodiments include a tracking system comprising a tracking probe assembly comprising a probe shaft with a depressible sliding shaft tip, and a mount with a trackable mobile stray marker at one end of the probe shaft, and a plurality of depth-stops at the opposite end of the probe shaft. Further, some embodiments include a dynamic reference frame coupled to the probe shaft adjacent the mount.

Some embodiments further comprise a tracking probe assembly comprising a probe shaft, a mobile marker that actuates via a depressible trigger, and at least one coupled dynamic reference frame including optically trackable markers.

Some embodiments include an anatomy analysis method comprising providing at least one trackable surgical tool including a tool dynamic reference frame and at least one trackable marker, where the at least one trackable surgical tool is configured so that any fixed or mobile portion of the at least one trackable surgical tool can be registered in 3D space. In some embodiments, the method includes providing at least one 3D tracking camera or imaging system configured to track the at least one trackable marker. In some embodiments, the method includes registering the location of one or more fiducial markers inside or outside a surgical site of the patient. In some embodiments, the method includes providing a processor and a memory coupled to the processor, where the memory stores anatomy contour measurement instructions executable by the processor to track 3D coordinates of one or more of the fiducial markers. In some embodiments, the instructions executable by the processor including outputting on a display an anatomical imaging analysis of at least a portion of the patient, and one or more registered anatomical landmarks that are adjusted in position and orientation relative to the registered contour.

Some embodiments of the invention include a trackable probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker. In some further embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a linkage arm link coupled to a slidable shaft, where the user actuable marker is coupled to the slidable shaft, and is configured and arranged to enable movement of the user actuable marker that is coaxial with the probe shaft when the linkage arm is actuated by user actuation of the trigger.

In some embodiments, the system further comprises a 3D tracking camera or imaging system configured to track the at least one trackable marker, and a processor and a memory coupled to the processor, where the memory stores anatomy contour measurement instructions executable by the processor to track 3D coordinates of at least one fixed or mobile marker, and output on a display an anatomical imaging analysis of at least a portion of a patient, and one or more anatomical landmarks and registered contour of the patient.

Some embodiments include a 3D trackable probe system comprising a probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft, and at least one 3D tracking camera or imaging system configured to track the at least one trackable marker. Some embodiments include a processor and a memory coupled to the processor, where the memory stores instructions executable by the processor to track 3D coordinates of one or more of trackable markers, and calculate a 3D position and pose of the probe assembly.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker.

In some embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a linkage arm coupled to a slidable shaft, where the user actuable marker is coupled to the slidable shaft, and is configured and arranged to enable movement of the user actuable marker that is coaxial with the probe shaft when the linkage arm is actuated by user actuation of the trigger.

In some embodiments of the method, the dynamic reference frame is attached to the patient. In some embodiments of the method, the dynamic reference frame is coupled to a surgical table or adjacent surface, where the dynamic reference frame is adjacent to the patient.

Some embodiments include a method of analyzing and providing a patient's spinal alignment information and therapeutic device data. In some embodiments, the method can comprise obtaining initial patient data, and acquiring spinal alignment contour information. In some embodiments, the method can comprise assessing localized anatomical features of the patient, and obtaining anatomical region data. In some embodiments, the method can include analyzing the localized anatomy and therapeutic device location and contouring. In some embodiments, the method can output localized anatomical analyses and therapeutic device contouring data on a display.

DESCRIPTION OF THE DRAWINGS

FIG. 1B illustrates a side view of a tapered, external-mating bone-mounted fiducial as described previously in relation to FIG. 1A in accordance with some embodiments of the invention.

FIG. 1C illustrates a frontal view of a tapered, external-mating bone-mounted fiducial as described previously in relation to FIGS. 1A-B in accordance with some embodiments of the invention.

FIG. 2B illustrates a frontal view of a 3D-tracked probe with its tracked mobile stray marker (TMSM) in an untriggered state as described previously in relation to FIG. 2A in accordance with some embodiments of the invention.

FIG. 2C illustrates a frontal view of a 3D-tracked probe with its TMSM in a triggered state as described previously in relation to FIGS. 2A-B in accordance with some embodiments of the invention.

FIG. 2D illustrates a perspective view of a 3D-tracked probe with its TMSM in an untriggered state. The probe is not engaged with the external-mating bone-mounted fiducial as described previously in relation to FIGS. 2A-C in accordance with some embodiments of the invention.

FIG. 2E illustrates a perspective view of a 3D-tracked probe with its TMSM in a triggered state. The probe is now engaged with the external-mating bone-mounted fiducial as described previously in relation to FIGS. 2A-D in accordance with some embodiments of the invention.

FIG. 4B-C illustrate perspective views of alternate designs for a tracking device to be fixated in MIS pedicle screws as described previously in relation to FIG. 4A in accordance with some embodiments of the invention.

FIGS. 4E-F illustrates a perspective view of the mating process of the tracking device to MIS percutaneous screws as described previously in relation to FIGS. 4A-D in accordance with some embodiments of the invention.

DETAILED DESCRIPTION

Figure 1A:
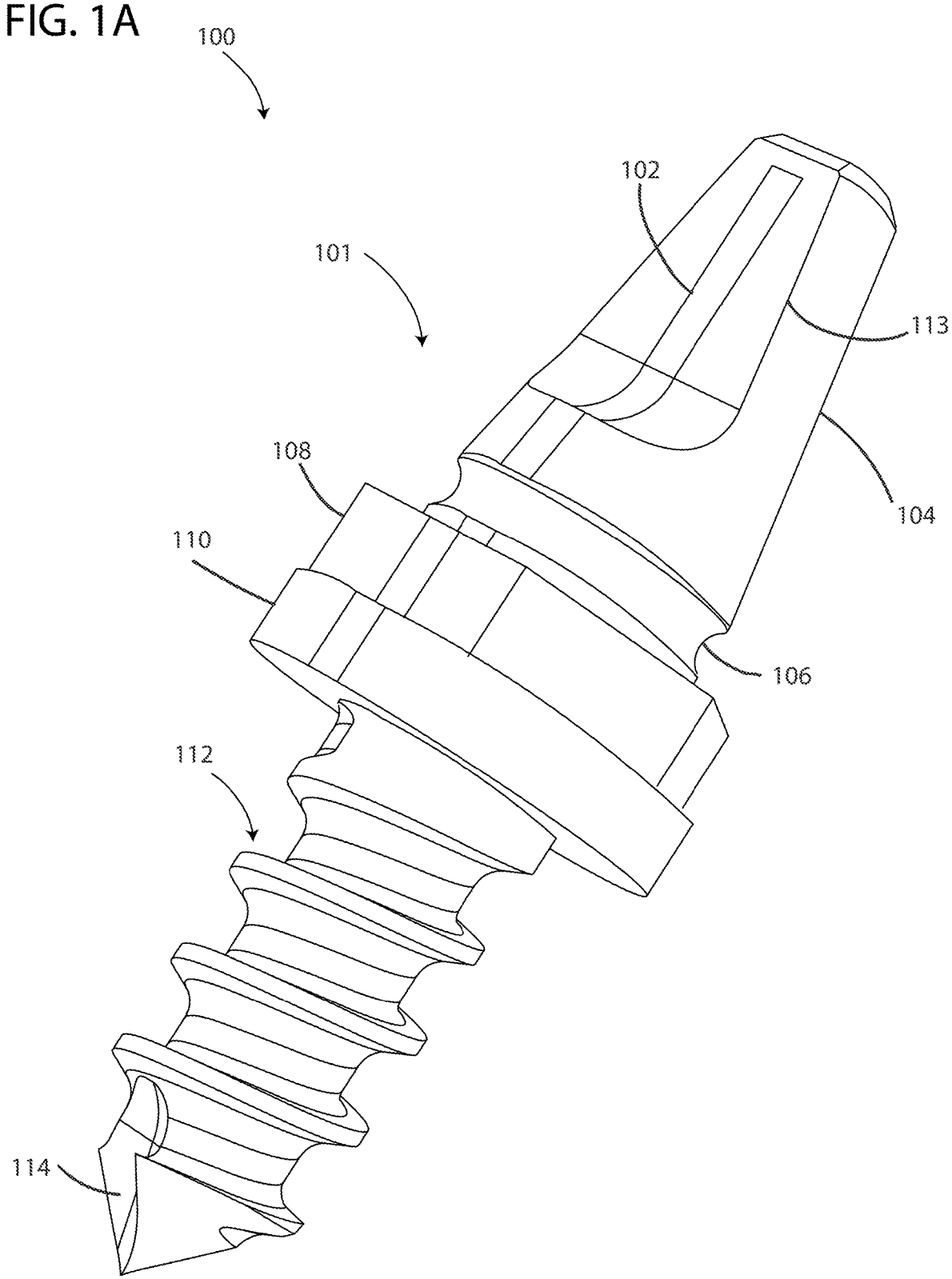
FIG. 1A illustrates a perspective view of a tapered, external-mating bone-mounted fiducial in accordance with some embodiments of the invention.

Before any embodiments of the invention are explained in detail, it is to be understood that the invention is not limited in its application to the details of construction and the arrangement of components set forth in the following description or illustrated in the following drawings. Some embodiments of the invention are configured to be combined with some other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, in some embodiments, the terms "mounted," "connected," "supported," and "coupled" and variations thereof are used broadly and encompass both direct and indirect mountings, connections, supports, and couplings. Further, in some embodiments, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to some embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

In some embodiments, "tracked" refers to the ability of a particular object to interface with a tracking device (e.g., one or more 3D-tracking optical cameras, robotic end effector, 2D camera, etc.) in at least FIGS. 1-4, that tracks the 3D coordinates of the tracked object relative to the tracking system's coordinate system. One example of an object that is "tracked" is when it possesses a substantially rigidly-attached dynamic reference frame that is tracked in 3D space.

In some embodiments, a dynamic reference frame (hereinafter "DRF") refers to three or more points (markers) that are positioned in a uniquely identifiable configuration such that their discrete locations are associated with an object identity. Some embodiments include uniquely-arranged markers that can allow for the calculation of both the 3D location and pose of a DRF. Some embodiments can also define a coordinate system relative to the DRF. In some embodiments, a stray marker refers to a 3D-tracked object, typically either light-reflective or light-emitting, which can be visualized by a 3D-tracking camera and is not one of the markers that define a DRF. In some embodiments, a stray marker can be associated with a DRF as well as have its location, pose, and behavior computed relative to one or more DRFs.

In some embodiments, a tracked mobile stray marker (TMSM) refers to a stray marker that is designed to move relative to either other stray markers or to nearby DRFs. In some embodiments, the computation of a TMSM's position and/or motion relative to those other entities can be interpreted to communicate information and/or commands to a computer acquisition system.

In some embodiments, a probe refers and/or defines a device that is tracked in such a way that its location, orientation, and identity are known in 3D space. In some embodiments, the system can extrapolate the location and orientation of other points and/or markers on and/or near the tracked object (e.g., the tip, shaft, unique features, etc.) even if they aren't directly tracked independently.

Some embodiments include a fiducial. In some embodiments, a fiducial can be an object that is used primarily as a reference to another point in space. In some embodiments, a fiducial can be placed near an object/region of interest. In some embodiments, the relative position of the fiducial to the object of interest can be initialized. In some embodiments, the location and orientation of the fiducial can be referenced in the future after initialization. In some embodiments, the precise location of the initialized object/region of interest can be calculated. In some embodiments, fiducials can have unique surface patterns in the form of indentations to be tapped, grooves to be traced, and/or mating features to be coupled. In some embodiments, the fiducial unique surface patterns can interact with a 3D-tracked probe or end-effector. In some embodiments, the fiducial's 3D location and orientation, as well as identity, can be calculated by the acquisition system. In some embodiments, a fiducial can be an object with embedded radiopaque markers, that enable for the fiducial's visualization and registration by radiographic imaging. Some embodiments include, a fiducial marker. In some embodiments, the fiducial maker can be used as an equivalent term to "fiducial", unless referring specifically to the embedded "radiopaque markers" within the fiducial structure that can be visualized on X-rays.

In some embodiments, the term "3D rigid transform" describes the mathematical operation that involves the computational application of a matrix containing both rotation and translation transformations. In some embodiments, the 3D rigid transform can be utilized when the system needs to transform the relations of an object from one coordinate axes to another, without deformation of the object. In some embodiments, an example can be: instead of having a 3D-tracked tool's location coordinates and orientation values to be in reference to a 3D-tracking acquisition system, the 3D-tracked tool can be substantially rigidly transformed to be in reference to the coordinates and orientation of another 3D-tracked tool or DRF within the scene. Further, some embodiments include "rigid body transform", a synonym.

Some embodiments include a pedicle screw. Some embodiments include a pedicle screw that can be inserted into the anatomical structure of a spinal vertebra called a pedicle. In some embodiments, the pedicle screw can be referenced. In some embodiments, the pedicle screw can be assumed that the system can be compatible with any other screws, fasteners, and/or other surgical implants (e.g., cages, rods, etc.).

In some embodiments, a tulip-head can be an object that attaches to a screw-head and can be polyaxial or uniaxial in its range of motion. In some embodiments, the tulip-head typically has internal threads that enable a fastener to engage substantially rigidly with the structure. In some embodiments, the tulip-head can have mating features on the external wall/surface that can enable a device to substantially rigidly attach to the tulip-head. In some embodiments, the tulip-heads can be designed to accept the insertion of a rod implant.

In some embodiments, a rod can be any object with a cross-section similar to a circle. Some embodiments include, additional shapes can include a keyhole, semi-circle, and the like. In some embodiments, a rod can be of any length and curvature. In some embodiments, a rod can be coupled to tracked and non-tracked tools. In some embodiments, a rod can be inserted into the cavity of a tulip-head and can be substantially rigidly fixed in-place via a cap screw that is fastened via threads on the interior wall of a tulip-head.

In some embodiments, register or a registration refers to any time a 3D-tracked tool or object signals information to the computer system regarding an object's state, 3D location, 3D orientation, unique identity, relative position to other objects, or other relevant information for the system's algorithms. Some embodiments include, for example: a 3D-tracked probe can register the position and identity of a fiducial, meaning that the 3D-tracked probe can communicate to the computer system that a particular fiducial can have a specific position and orientation in 3D space relative to the 3D-tracking, acquisition system.

In some embodiments, "sagittal" is an anatomical plane that refers the side view of a patient in which the superior portion of the patient (e.g., the head) is on the right or left side and the inferior portion of the patient (e.g., feet) is on the opposite end, depending on which side of the patient the perspective is from, left or right half. In some embodiments, the posterior aspect of the patient will be visible on either the top or bottom of the view, depending on whether the patient is supine or prone.

In some embodiments, "coronal" is an anatomical plane that refers to the top view of a patient in which the superior portion of the patient (e.g., the head) is on the top or bottom and the inferior portion of the patient (e.g., feet) is on the opposite end, depending on which side of the patient the perspective is from, below or above, as well as which side the left or side of the patient appears in view, right or left.

In some embodiments, "axial" is an anatomical plane that refer to the cross-sectional view of a patient in which the posterior portion of the patient is on the top or bottom and the anterior portion of the patient is on the opposite end, depending on which side of the patient the perspective is from, prone or supine. In some embodiments, the patient view can also change depending on whether the view is pointed towards the inferior or superior aspect of the patient. In some embodiments, "transverse" can be used. In some embodiments, transverse can be an equivalent term to "axial".

In some embodiments, "depressible sliding shaft" or "plunger" refers to a depressible, sometimes spring-loaded, sliding shaft that actuates via pressing against a surface, a spring-loaded button, or other mechanical means of actuation. In some embodiments, a plunger can have a mechanically-linked TMSM that can communicate its position along the plunger relative to the position of a nearby DRF or other tracked stray markers. In some embodiments, the shaft can be coaxial with a 3D-tracked tool. In some embodiments, the shaft does not need to be protruding out of an object. In some embodiments, the shaft can be engaged within an object.

In some embodiments, spinal alignment parameters of an assessment of the segmental and/or full-length spinal alignment can be produced with values for each relevant radiographic alignment parameter (e.g., Cobb angle, lumbar lordosis (LL), thoracic kyphosis (TK), C2-C7 sagittal vertical axis (SVA), C7-S I SVA, C2-S I SVA, central sacral vertical line angle or horizontal offset (CSVL), T1 pelvic angle (TIPA), upper instrumented vertebra pelvic angle (UIV-PA), pelvic tilt (PT), pelvic incidence (PI), chin-brow to vertical angle (CBVA), T1 slope, sacral slope (SS), C1-2 lordosis, C2-C7 lordosis, CO-C2 lordosis, C1-C2 lordosis, PI-LL mismatch, C2-pelvic tilt (CPT), C2-T3 angle, spinopelvic inclination from T1 (T1 SPi) and T9 (T9SPi), CO slope, mismatch between T-1 slope and cervical lordosis (T1 S-CL), and/or global sagittal angle (GSA)). Additionally, any time alignment assessments or calculation of alignment parameters are mentioned in this document, it can be assumed that any of the above parameters, and others not mentioned but commonly known, can be calculated in that portion of the description.

In some embodiments, a 3D-tracking acquisition system can refer to the use of a 3D-tracking system to acquire points in 3D space and register particular commands via 3D-tracked tools. Some embodiments include, for example: an optical-tracking system that can be used in surgical navigation (e.g., NDI Polaris Spectra stereoscopic camera system, which tracks tools or objects, as depicted in FIG. 126, FIG. 127, etc.).

In some embodiments, a 3D-tracked probe is a tool that can be handheld or robot-held, and can be tracked in 3D physical space by any 3D-tracking acquisition system, such as an optical surgical navigation system (e.g., NDI Polaris stereoscopic camera). In some embodiments, relying on an optical surgical navigation system can include a probe with a substantially rigidly-attached, 3D-tracked DRF. Some embodiments can include the inclusion of a mechanically-linked, 3D-tracked mobile stray marker (TMSM) that can be mounted on, or coupled with, a depressible, spring-loaded, and/or user-actuated shaft that can actuate the motion of the TMSM either linearly or rotationally (e.g., about a hinge pivot on the probe).

In some embodiments, an optical, 3D-tracking system can refer to any optical system that can provide a 3D mapping or image of a scene or calculate the location, orientation, and identity of a tracking-compatible object. Some embodiments include, for example: a 3D-tracking system can be a surgical navigation system (e.g., an NDI Polaris Spectra® stereoscopic camera system, from NDI International, 103 Randall Drive, Waterloo, Ontario, Canada N2V 1C5.). In some embodiments, similar information can be gathered from any 3D-tracking, optical-based system.

In some embodiments, a display monitor refers to any display embodiment that can visually depict the output of the system, its feedback systems and instructions, its calculations, and other relevant information or settings that are available.

In some embodiments, an acquisition system is synonymous with the 3D-tracking acquisition system term described above. In some embodiments, this system is a 3D-tracking camera (e.g., NDI Polaris Spectra® stereoscopic camera) and the computer system with which it is communicating.

In some embodiments, an end-effector refers to any component of an object that interfaces with another surface or object in a manner that enables the registration or communication of information including, but not limited to: 3D location, 3D orientation, unique identity, physical or identity-based relations to other objects in a scene, forces applied to an object or forces experienced by an end-effector, and the like. Some embodiments include, for example: a 3D-tracked distal tip of a robotic arm.

In some embodiments, a tracing refers to the method of acquiring discrete or continuous points along a surface via a 3D-traced probe or object.

In some embodiments, an endplate refers to the surface of a spinal vertebra that interfaces with the intervertebral disc and the nearby vertebra coupled on the other side of the intervertebral disc. In some embodiments, the endplate can be a common anatomical landmark used for measuring the spinal alignment parameters of a patient (e.g., Cobb angles), mainly due to the way that an endplate surface X-ray can be utilized to represent an anatomical line segment or vector, from which two or more endplates can be used to calculate relative angles between two or more vertebrae (e.g., LI and SI endplate measurements can be used to calculate the lumbar lordosis angle of the patient's lumbar spine).

In some embodiments, pose refers to the orientation of an object with respect to another object or 3D-tracking acquisition system. In some embodiments, the pose of an object can be redundant from multiple perspectives or it can be unique and identifiable in a way that it distinguishes itself from other objects. In some embodiments, the pose of an object can be outputted via 3D orientation values (e.g., quaternions, Euler angles, rotation matrices, series of vectors, etc.).

In some embodiments, the term "unique" can refer to the distinct identity of an object, or its distinguishable configuration, position, or orientation. In some embodiments, the phrase "unique pattern" can refer to an asymmetric or identifiable arrangement of objects that can be registered in a manner that the group of objects can be identified uniquely compared to another group of tracked/registered objects.

In some embodiments, "level" refers to a specific spinal vertebra within the span of the vertebrae of the spinal column. In some embodiments, a level can refer to any of the vertebrae (e.g., LS, TIO, C1, S3, etc.). In some embodiments, the abbreviations of the sections of the spinal vertebrae can be: lumbar (L), thoracic (T), cervical (C), and sacral (S) vertebrae.

In some embodiments, "fully engaged" can be used to describe two or more objects that are completely linked, mated, coupled, adhered, joined, fastened, or aligned. In some embodiments, two or more objects can be fully engaged. In some embodiments, the computer system can record an event, collect information, acquire 3D locations or orientations, determine the identity of one or more objects, receive a command, or output information regarding the engagement. In some embodiments, fully-engaged objects can trigger a communication to the computer system of a particular command or acquisition to store.

In some embodiments, a "trigger" can be used to describe either a button or a moment of communication that signals to the computer or acquisition system to store data, output calculations or other relevant information, interpret a command, or register an object's identity.

Some embodiments can be independent inventions and do not have to be precluded by other inventions or categorical system workflows (e.g., patient initialization, alignment contour acquisition, etc.). For example, some embodiments of the invention described herein include devices, assemblies, systems, and methods to assess the intraoperative alignment of the spine, extract information as to the contour or alignment of instrumented hardware, and evaluate some of the biomechanical qualities of the patient's spine. Some embodiments of the overall system are a central software system can receive inputs from discrete and/or continuous location data (e.g., inside and/or outside of the surgical site), where the data is gathered by non-radiographic or radiographic systems, algorithmic calculations, or manual user-based interactions, to generate visual and quantitative outputs relating to the intersegmental or full-length alignment, curvature, position, range-of-motion, and biomechanical flexibility of the patient's spine.

In some embodiments of the invention, current spinal alignment measurements during surgery are compared to measurements from a large database of prior patients with similar indications and surgical procedure types to identify how the current measurements correspond with data-driven success outcomes for surgical corrections. In some embodiments, the system compares the current patient's demographics and current alignment measurements to normative and historical databases. Some embodiments of the invention enable prior measurements acquired preoperatively or from prior surgeries to be compared to current alignment measurements. In some embodiments, the surgeon can stratify the available database comparison by time period (e.g., last 5 years, last 1 year, last 6 months), surgeon's colleagues (e.g., within the same hospital or within other hospital systems), thresholds for success set by trusted specialty groups (e.g., international spine study group), key opinion leaders in the field (e.g., match to similar patients that identified 'experts' have previously operated on), all patients, etcera. In some embodiments, the system stratifies the database according to the type of surgical approach currently being attempted (e.g., posterior open fusion from T12 to pelvis). In some embodiments, machine learning algorithms such as support vector machines, deep-learning, decision forests, convolutional neural networks, etc., can be applied to the above discussed input variables of the database to aid in predicting how the patient may appear after surgery and assessing standing balance alignment parameters (e.g., predicting SVA, PT, SS, LL, TK, etc.). In some embodiments, the system constantly updates the database according to new surgeries and patient data profiles that are submitted into the system, further enabling the algorithms to fine tune hyperparameters for optimal accuracy of predictive analytics, including preoperative planning recommendations, intraoperative report card analyses, and postoperative feedback on achieved results.

Some embodiments of the invention include a 3D-tracked probe and bone-mounted fiducial which when used together can continuously update the registration of anatomical landmarks of interest without the need for excessive X-Ray imaging or workflow delays. In some embodiments, the fiducial marker can rigidly attach to any bony anatomical landmark in the body and serves as a registerable marker that, once initialized, can provide the 3D location and pose of any component of the landmark (e.g., vertebral endplate, femoral head centroid, etc.) without the need for additional imaging. In some embodiments, initialization of the fiducial marker can be achieved via 2D or 3D X-Ray images or via state-of-the-art image-guided navigation workflows. In some embodiments, the fiducial's location and pose can be registered with a 3D-tracked probe, 3D-tracked DRF, robotic end effector, optical scanner, or any other localization tool.

In some embodiments, FIG. 1A 100 illustrates a fiducial marker device 101 with a registration surface and bone-fixation features (e.g., self-tapping screw threads). In some embodiments, the fiducial marker utilizes screw threads 112 to rigidly attach to a bony landmark of interest. In some embodiments, the screw threads 112 involve a self-tapping or self-cutting flute that enables for rapid fixation of the device to bone without the need for pre-drilling or other preparation steps. In some embodiments, the fiducial also comprises an asymmetric, unique registration interface. In some embodiments, the fiducial's registration interface is a tapered, cylindrical protrusion with a back surface 104 and a keyed front surface 113, which includes an orientation indicator 102 to be used during mating with a 3D-tracked probe or X-Ray initialization adapter (not shown). In some embodiments, the fiducial device only enables for registration from one precise 3D pose. In some embodiments, the fiducial device's mating surface includes an undercut neck 106 that enables for additional fixation to a registration device. In some embodiments, the fiducial device includes a hexagonal surface 108 and a depth-stop surface 110 that enable for both fixation to a registration device and/or a screwdriver.

In some embodiments, FIG. 1B 120 and FIG. 1C 125 illustrates side views of the fiducial marker device 101 with a registration surface and bone-fixation features (e.g., self-tapping screw threads). In some embodiments, the orientation indicator 102 can be aligned on the front face 113 of the fiducial to enable visual guidance to the user for aligning the fiducial with a registration device during the mating and registration process.

Figure 2A:
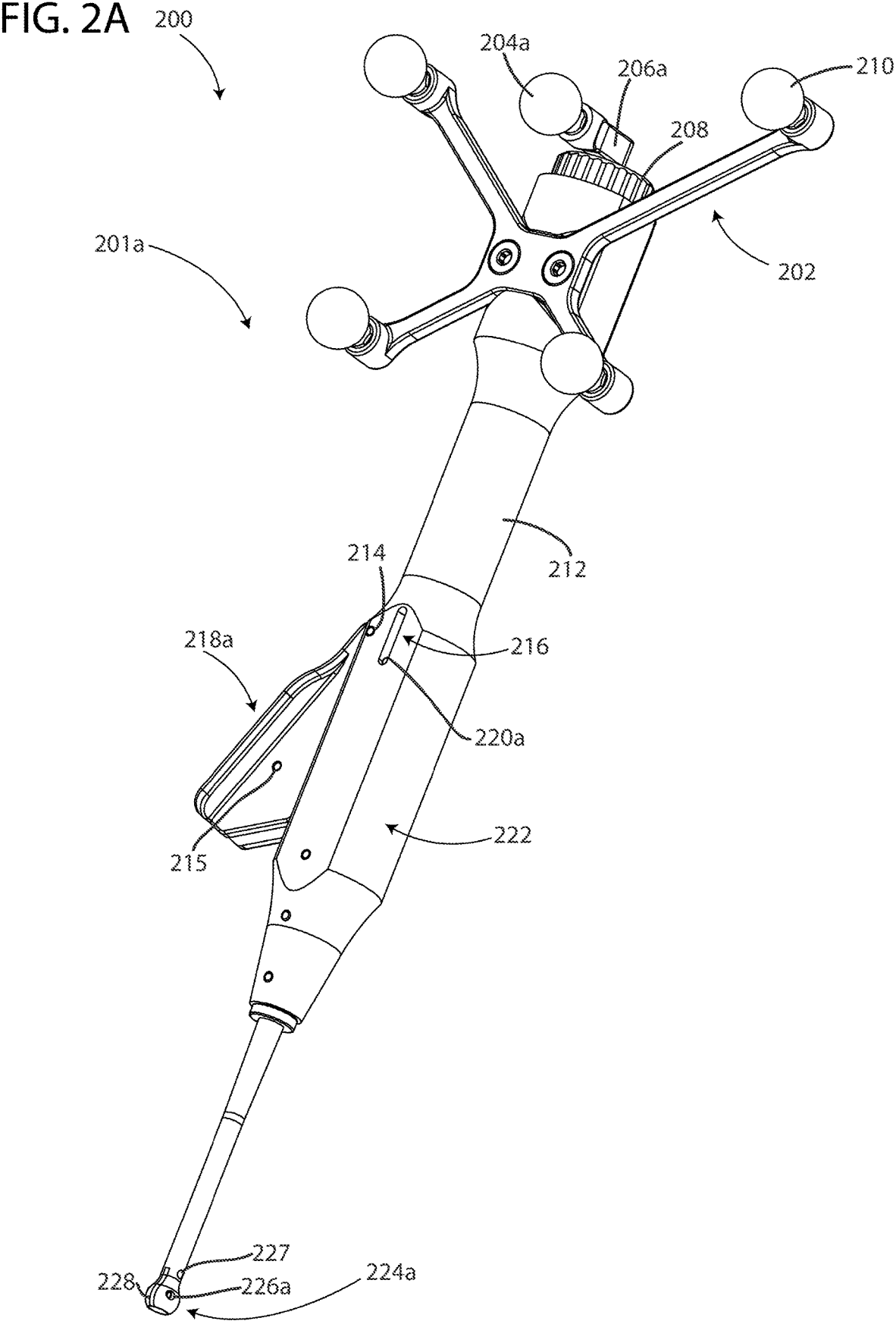
FIG. 2A illustrates a perspective view of a 3D-tracked probe with an internal-mating probe tip that uniquely mates with a bone-mounted fiducial, in accordance with some embodiments of the invention.
Figure 2F:
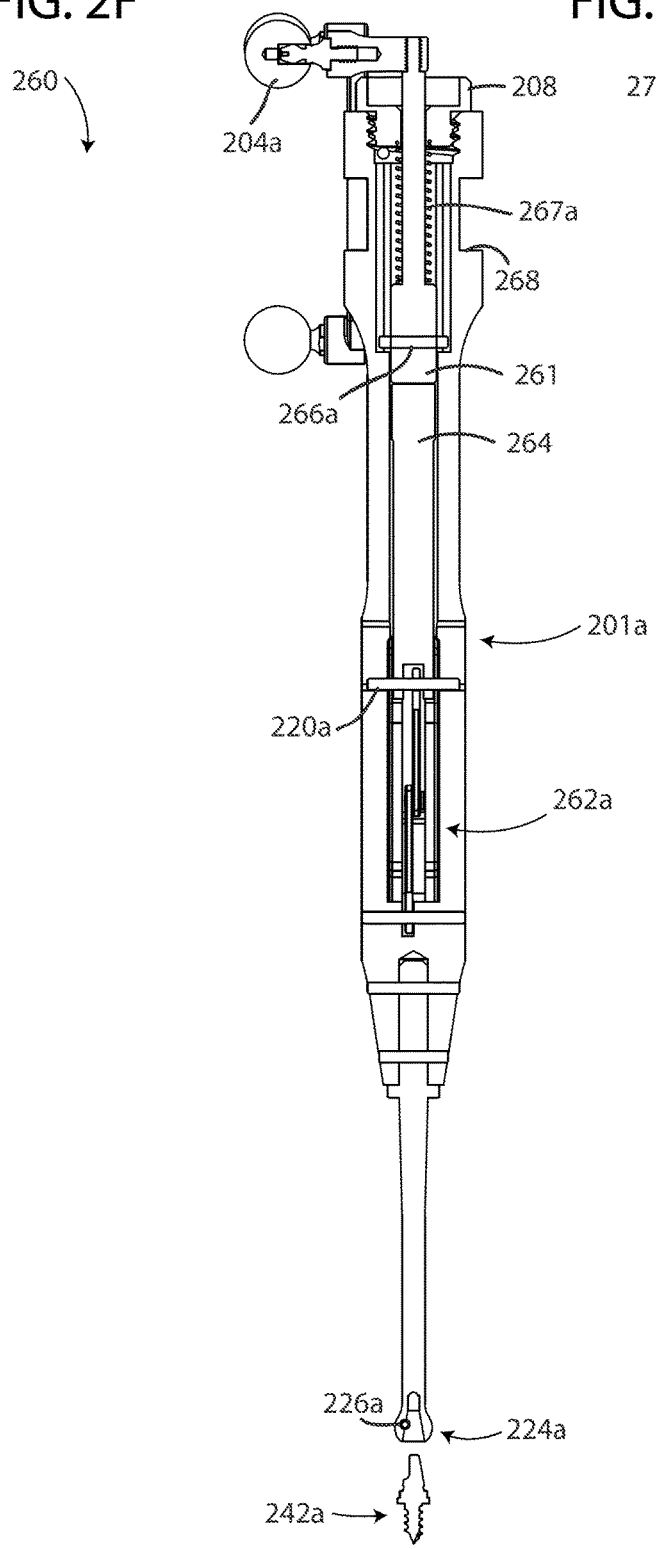
FIG. 2F illustrates a side cross-sectional view of a 3D-tracked probe with its TMSM in an untriggered state. The probe is not engaged with the external-mating bone-mounted fiducial as described previously in relation to FIGS. 2A-E in accordance with some embodiments of the invention.
Figure 2G:
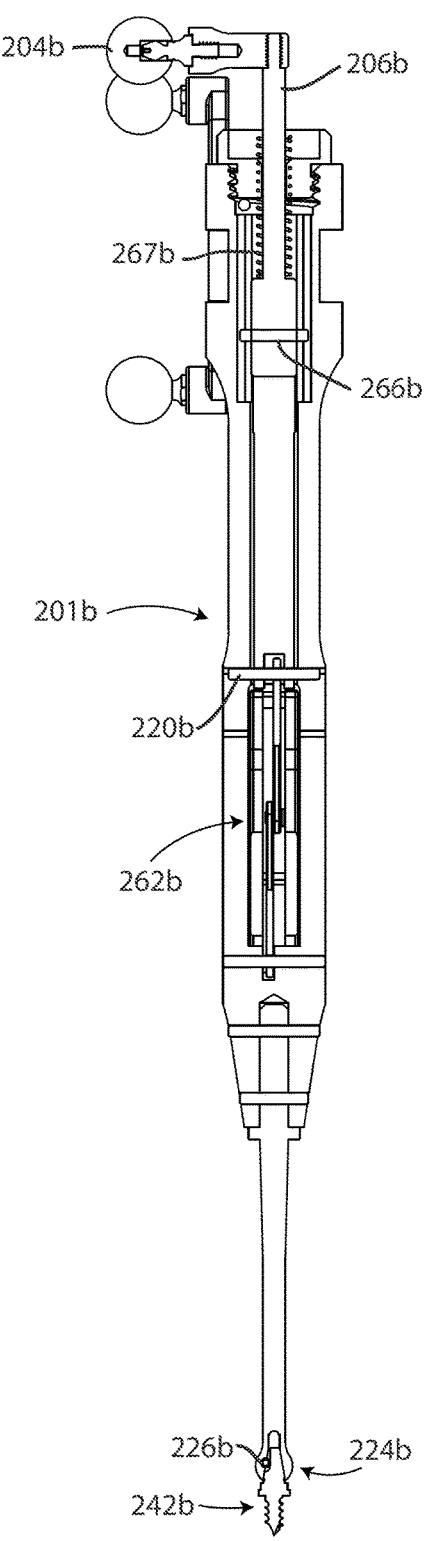
FIG. 2G illustrates a side cross-sectional view of a 3D-tracked probe with its TMSM in a triggered state. The probe is now engaged with the external-mating bone-mounted fiducial as described previously in relation to FIGS. 2A-F in accordance with some embodiments of the invention.

In some embodiments, FIG. 2A 200 illustrates a 3D-tracked probe that can be used to register continuous or discrete points along a surface (e.g., patient anatomy, surgical table, fiducial device) and mate with a fiducial marker device that has a complementary mating interface for the probe's tip feature. In some embodiments, the 3D-tracked probe 201a comprises a shaft 212, trigger button (undepressed) 218a, 3D-tracked DRF 202 that contains a unique configuration of three or more 3D-tracked markers 210, TMSM (undepressed) 204a, TMSM mount (undepressed) 206a, and a probe tip 224a (disengaged), which includes an orientation indicator 228, cleaning flush port 227, and a fiducial-engaging cross pin (disengaged) that defines the keyed orientation of the female conical surface (not shown) of the probe tip. In some embodiments, the probe's female, fiducial-mating interface is also tapered, like the fiducial's tapered male registration interface. In some embodiments, this process enables for rapid, yet still accurate, registration of the fiducial with less pressure on the user to accurately align the two devices for the mating process. In some embodiments, the trigger button (undepressed) 218a includes a cross pin 215 that engages with an internal probe linkage system (not shown) to depress the TMSM 204a via the actuation of the TMSM mount interface 206a. In some embodiments, the trigger button 218a pivots about a pivot pin 214, and the internal linkage system (not shown) is restrained in its distance of travel via a cutout guide 216 that restricts movement of an actuation pin 220a that is mechanically linked to the trigger button 218a and TMSM mount 206a. In some embodiments, the probe has one or more surface features along the shaft 212 that enable user-friendly regions to hold the probe in a comfortable manner during use. In some embodiments, the probe includes a twistable knob 208 at the top end of the probe which when disengaged allows for the cleaning of the probe's internal shaft surface for ease of sterilization.

In some embodiments, FIG. 2B 230 and FIG. 2C 235 illustrate assemblies of the 3D-tracked probe in an "inactive" or "active" state. In some embodiments, the 3D-tracked probe (inactive) 201a has a depressible trigger button 218a in the inactive state. In some embodiments, the 3D-tracked probe (active) 201b has a depressible trigger button 218b in the active state, in which the actuation pin 220b is mechanically raised into its fully depression position and the internal linkage mechanism (not shown) raises the TMSM mount 206b that is attached to the TMSM (active state) 204b. In some embodiments, once the trigger is depressed, the system calculates the TMSM's 204b relative positive from the DRF 202 and determines if its 3D location relative to the origin of the DRF 202 is beyond a determined threshold to define the probe to be in an active state.

In some embodiments, FIG. 2D 240 and FIG. 2E 250 illustrate an assembly of the 3D-tracked probe engaged with a fiducial marker device. In some embodiments, the user depresses the trigger 218b and actuates the rigidly-linked TMSM 204b far enough from the DRF 202 for the system to automatically determine that the probe's state is now "active" and to record the 3D location and pose of the fiducial 242b. In some embodiments, the probe tip 224b fully engages with the fiducial device 242b in a female-male, unique mate via a conical-stacking interface that includes a mating cross pin 226b that fully engages with the front face of the fiducial device 242b.

In some embodiments, FIG. 2F 260 and FIG. 2G 270 illustrate cross-sectional view of an assembly of a 3D-tracked probe and a fiducial device. In some embodiments, the probe (disengaged) 201a comprises an internal linkage mechanism 262a that is linked to an actuation pin 220a which actuates a primary shaft 264 and secondary shaft 261, which includes an orientation-locking pin (undepressed) 266a that compresses a spring (uncompressed) 267a against a twist knob 208. In some embodiments, the secondary shaft 261 is mechanically linked to the TMSM (inactive) 204a. In some embodiments, the probe (engaged, active) 201b comprises an internal linkage mechanism 262b that is actuated by the depressible trigger (not shown) 218b and which actuates the actuation pin 220b. In some embodiments, the secondary shaft and the orientation-locking pin (depressed) 266b compress the internal spring mechanism (compressed) 267b and elevate the TMSM mount (actuated) 206b and the attached TMSM (active) 204b. In some embodiments, the depressible trigger button (not shown) 218b is depressed when the probe (engaged, active) is fully engaged with the fiducial marker device 242b via the internal mating features of the probe tip 224b and its keyed cross pin 226b mechanism. In some embodiments, the probe tip contains a tapered, female fiducial-mating interface that can accept a wider range of 3D orientations for initial mating between the probe and fiducial to commence, and then the tolerance between the probe's mating interface and the fiducial's mating interface gets much smaller and ensures an accurate, reliable registration. In some embodiments, the fiducial's tapered mating interface can involve a variety of possible draft angles and divisions of the taper to ensure reliable mating. In some embodiments, the fiducial's tapered mating interface is tightly encapsulated by the probe's mating interface to ensure very little wobble and robust reliability for mating the two devices together many times. In some embodiments, a long shaft or pin is used to attach a fiducial marker to an underlying bony landmark of interest via a percutaneous, minimally-invasive approach in which the long shaft traverses layers of tissue until the fiducial can securely engage the bony anatomy.

Some embodiments of the invention involve using a bone-mounted fiducial to re-register anatomical landmarks, which are already being tracked using image-guidance navigation, after their 3D-tracked DRF is manipulated out of its intended position. In some embodiments, typically in image-guidance navigation (e.g., CT guidance), the navigation system is relying on the careful 3D-tracking of a DRF, attached to one or more anatomical structures (e.g., pelvis, vertebrae, femur, etc.), that is registered to those underlying anatomical structures in a particular relative position. In some embodiments, as the DRF moves, typically due to the patient's movement or the user manipulating the spine, the system adjusts the view of surgical instruments relative to the volumetric or 2D imaging that they are being tracked relative to. In some embodiments, if the DRF is bumped or manipulated, the traditional image-guided navigation is no longer accurate or safe, and the system will need to redo its navigation initialization process. In some embodiments, this invention can eliminate the need for additional imaging or navigation re-initialization processes by rigidly attaching a fiducial marker to the anatomy before the navigation system is initialized and can thus provide a reliable recovery of navigational guidance at any time during surgery after its first initialization.

Some embodiments of the invention involve using an X-Ray initialization adapter device to initialize a bone-mounted, or skin-mounted, fiducial device relative to anatomical landmarks of interest via X-Ray or volumetric imaging. In some embodiments, the X-Ray adapter device has a unique mating interface (female) that enables for mating with a fiducial mating interface (male) in only one unique 3D configuration. In some embodiments of the invention, the X-Ray adapter device's fiducial-mating interface can be further enhanced with additional mechanisms (e.g., cam lock, spring-loaded detent, wire protrusion, cross pin, indent to receive spring-loaded detent, etc.) to reduce the tolerance with the fiducial of interest and maximize repeatability of the initialization process.

Figure 3A:
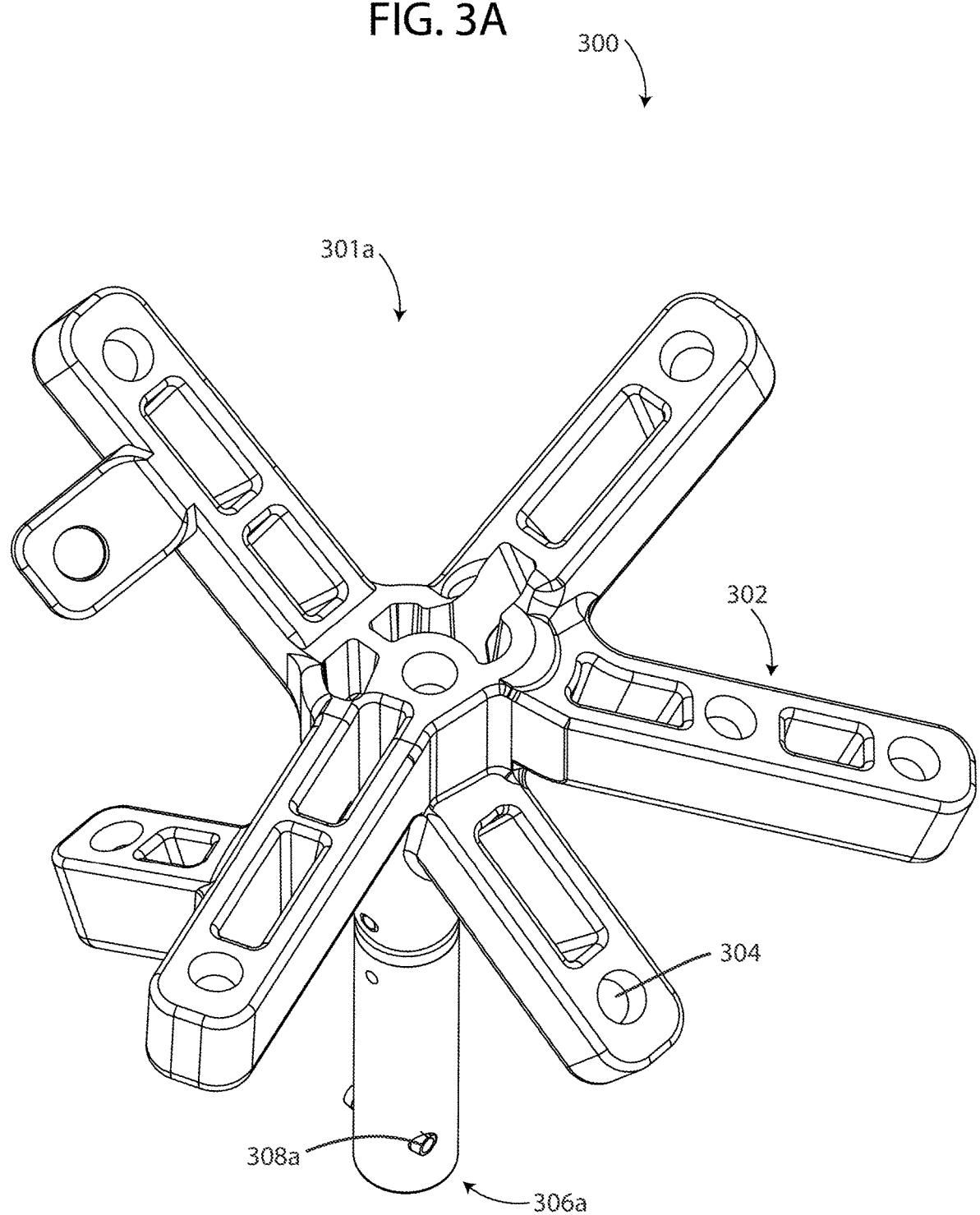
FIG. 3A illustrates a perspective view of an internal-mating XRay initialization adapter to the bone-mounted fiducial in accordance with some embodiments of the invention.

In some embodiments, FIG. 3A illustrates an assembly view 300 of an X-Ray adapter device equipped with a plurality of radiopaque markers and a fiducial-mating interface. In some embodiments, the X-Ray adapter device (disengaged) 301a comprises a device body 302, fiducial-mating interface 306a with an internal female mating surface (not shown) and an engaging cross pin (disengaged) 308a, and embedded radiopaque markers 304. In some embodiments, once the female mating interface and the cross pin (disengaged) 308a are fully engaged with the fiducial device (not shown), the X-Ray initialization adapter device is ready to be initialized with 2D or 3D X-Ray imaging.

Figure 3B:
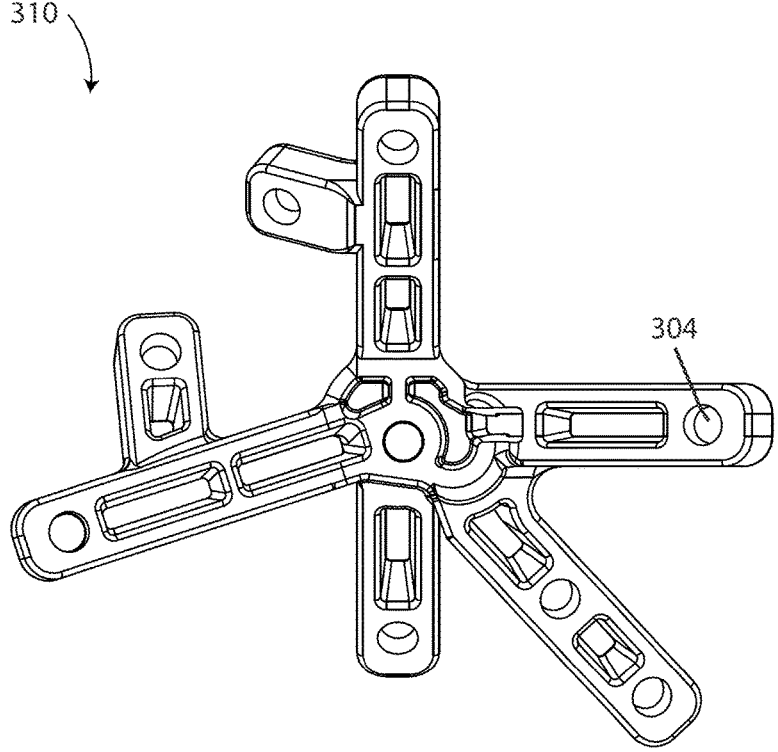
FIG. 3B illustrates a top view of an internal-mating XRay initialization adapter to the bone-mounted fiducial as described previously in relation to FIG. 3A in accordance with some embodiments of the invention.
Figure 3C:
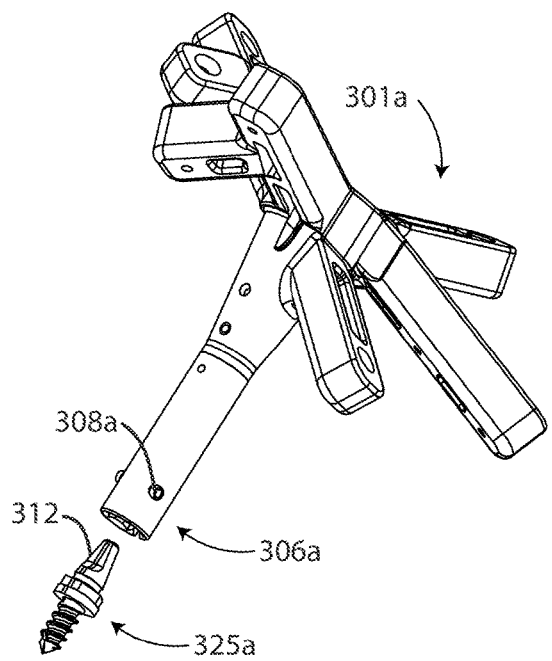
FIG. 3C illustrates a perspective view of an internal-mating XRay initialization adapter, not engaged with a bone-mounted fiducial as described previously in relation to FIGS. 3A-B in accordance with some embodiments of the invention.
Figure 3D:
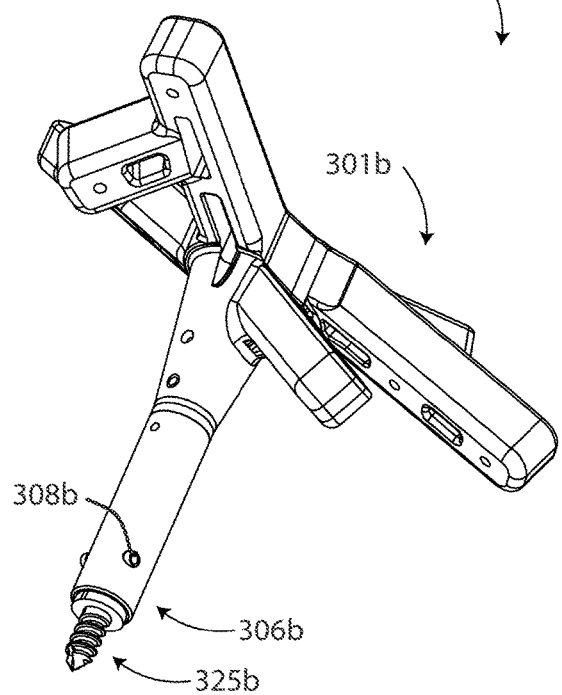
FIG. 3D illustrates a perspective view of an internal-mating XRay initialization adapter, engaged with a bone-mounted fiducial as described previously in relation to FIGS. 3A-C in accordance with some embodiments of the invention.
Figure 3E:
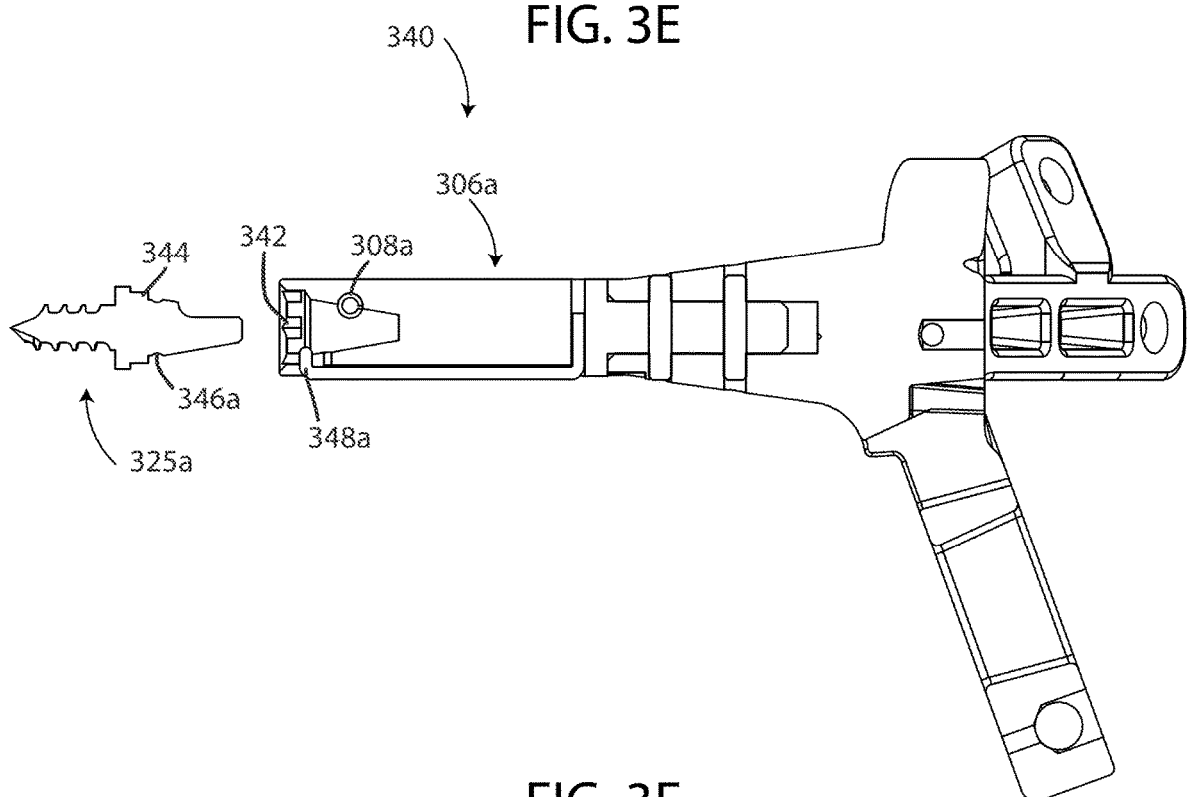
FIG. 3E illustrates a side cross-sectional view of an internal-mating XRay initialization adapter not engaged with a bone-mounted fiducial as described previously in relation to FIGS. 3A-D in accordance with some embodiments of the invention.
Figure 3F:
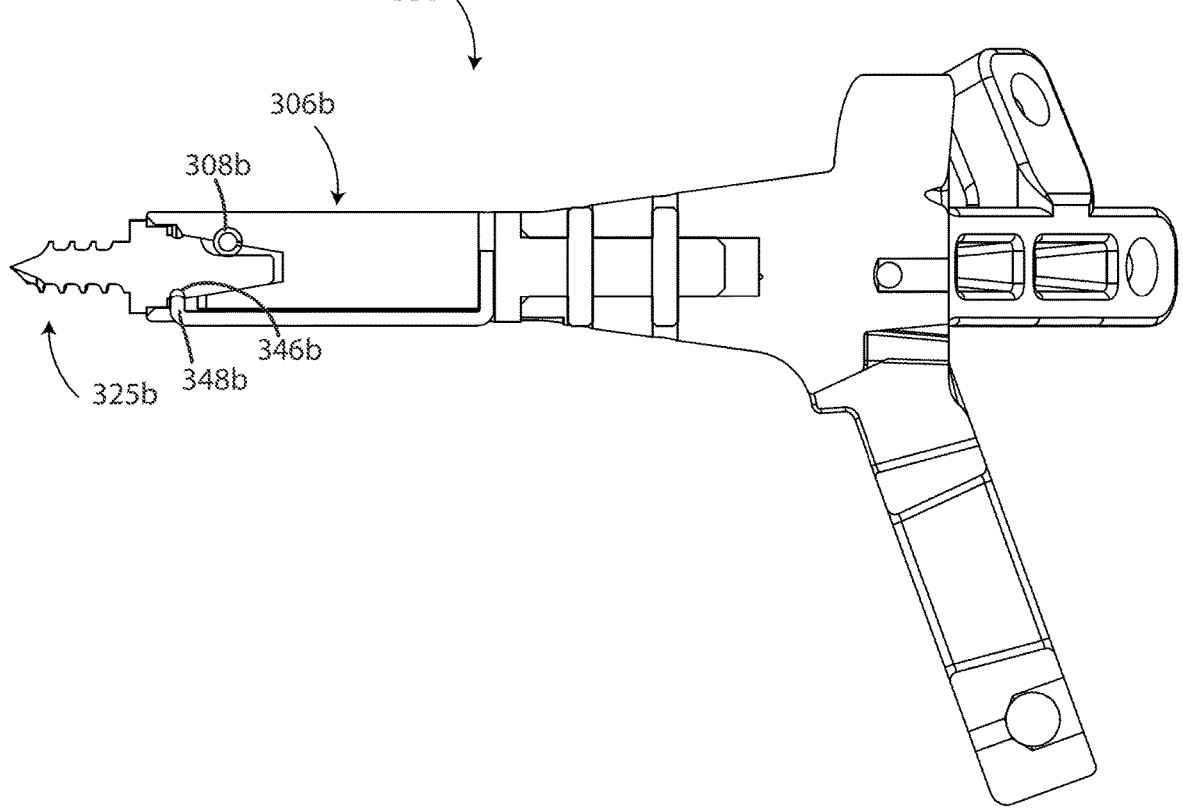
FIG. 3F illustrates a side cross-sectional view of an internal-mating XRay initialization adapter engaged with a bone-mounted fiducial as described previously in relation to FIGS. 3A-E in accordance with some embodiments of the invention.

In some embodiments, FIG. 3B illustrates an assembly view 310 of an X-Ray adapter device. In some embodiments, FIG. 3C 320 and FIG. 3D 330 illustrate assemblies between an X-Ray initialization adapter device and a fiducial marker device. In some embodiments, the X-Ray adapter device (engaged) 301b substantially rigidly mates with the bone fiducial (registered) 325b via a unique mating interface between the X-Ray adapter device's mating tip (engaged) 306b which includes a keyed mating pin 308b. In some embodiments, the mating pin 308b can be a compressible spring pin, non-compressible pin, detent ball, or any combination of the aforementioned features.

In some embodiments, FIG. 3E 340 and FIG. 3F 350 illustrate cross-sectional views of assemblies of the X-Ray adapter device engaging with the bone fiducial device. In some embodiments, the X-Ray adapter device comprises a spring-loaded wire (disengaged) 348a, mating features for attaching to a hexagonal driver surface 342, and keyed cross pin (disengaged) 308a. In some embodiments, the fiducial device (registered) 325b is fully engaged with the X-Ray adapter (engaged) 306b when the spring-loaded wire (engaged) 348b is seated against the fiducial device's undercut feature 346b and the front face of the fiducial device is engaged with the X-Ray adapter's keyed cross pin (engaged) 308b.

In some embodiments, the X-Ray adapter device contains an array of embedded radiopaque markers. In some embodiments, the X-Ray adapter device 306b has an array of embedded radiopaque markers (e.g., 9 spheres), of which one or more of them are utilized as a redundant backup sphere in case one or more spheres are occluded during the X-Ray imaging registration process. In some embodiments, if one or more radiopaque markers are occluded during the imaging process, the remaining spheres that can be visualized will be sufficient for reliable, accurate image-based registration. In some embodiments, the array of embedded radiopaque markers is designed to avoid occluding each other during imaging, and also have an asymmetric configuration that prevents several spheres from being co-linear and subsequently introducing indefinite solutions to the image registration process.

Some embodiments of the invention involve using an X-Ray adapter device to initialize a bone-mounted fiducial relative to multiple anatomical landmarks of interest via X-Ray or volumetric imaging. In some embodiments, when a user wishes to register multiple anatomical landmarks relative to individual bone-mounted fiducials, a single X-Ray adapter device can be used to register each anatomical landmark to its attached fiducial marker via two or more X-Ray images. In some embodiments, one X-Ray adapter device with an array of embedded radiopaque markers can register a group of spinal vertebrae, each with their own attached, bone-mounted fiducial. In some embodiments, the X-Ray adapter device is mated to one of the bone-mounted fiducials, attached to one of the unregistered landmarks (e.g., L3 vertebra), for each group of anatomical landmarks (unregistered) that can fit in a single X-Ray image.

Some embodiments of the invention involve a 3D-tracked implant driver that tracks the real-time 3D location and actuation (e.g., expansion, pivoting) of an implant (e.g., interbody cage). In some embodiments, the 3D-tracked driver tracks only one actuation mechanism (e.g., expansion, pivoting, splitting, etc.). In some embodiments, the 3D-tracked implant driver can track multiple actuations, as illustrated below in relation to FIG. 4. In some embodiments, whether or not the implant is being tracked or not during insertion, 3D-tracked DRFs on each implant-interfacing anatomical landmark of interest can provide real-time feedback about the spine's dynamic changes of spinal alignment during the implantation process.

Figure 4A:
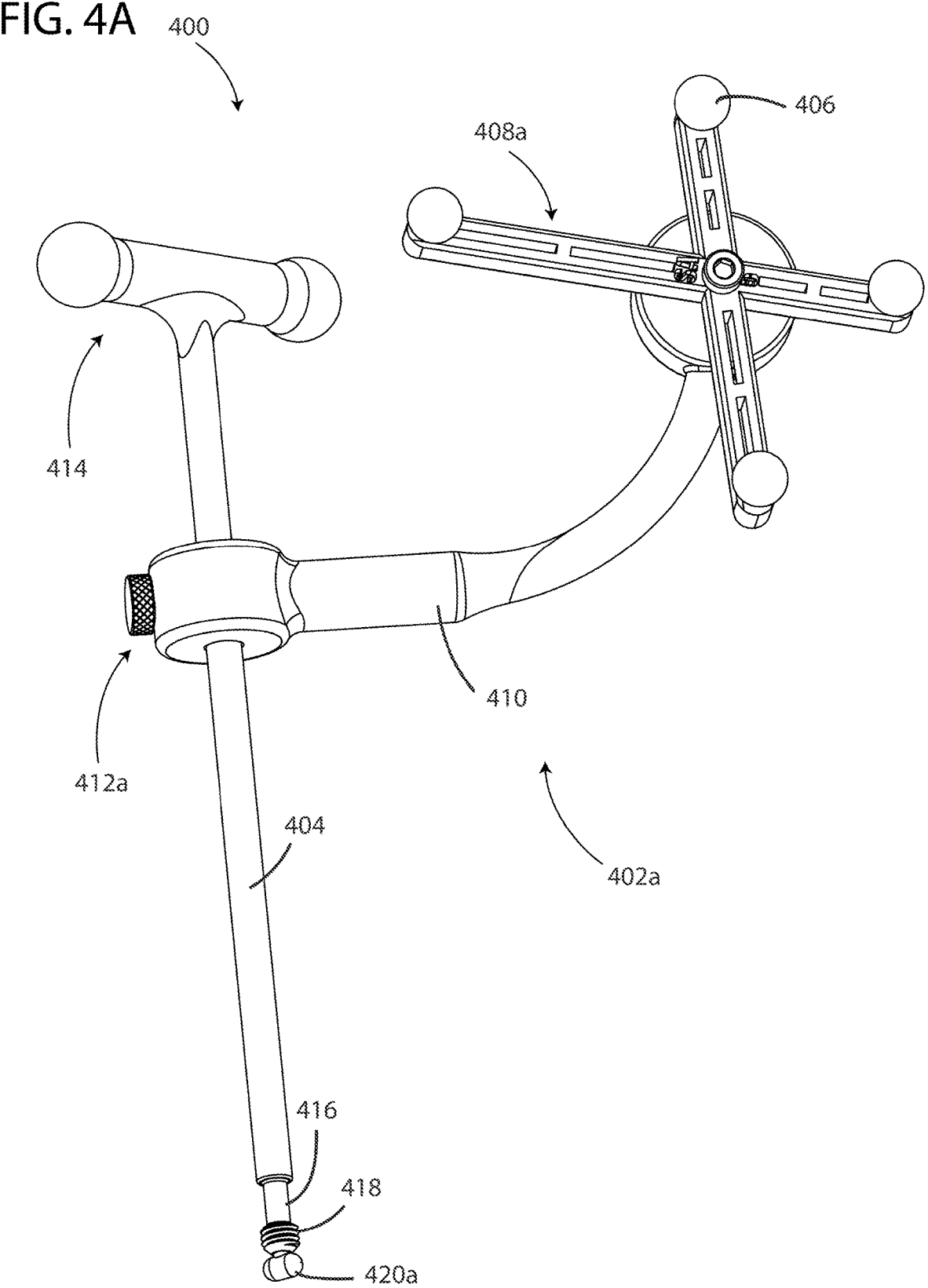
FIG. 4A illustrates a perspective view of a tracking device to be fixated to pedicle screw towers used in minimally invasive surgical (MIS) procedures in accordance with some embodiments of the invention.

In some embodiments, FIG. 4A illustrates an assembly view 400 of a 3D-tracked screw-locking device that can substantially rigidly lock the motion of a pedicle screw (not shown) and track the motion of an engaged vertebra of interest. In some embodiments, the 3D-tracked, screw-locking device (disengaged) 402a comprises of a shaft 404, handle 414, internal shaft tip 416, set screw 418, and screw-locking rod interface (disengaged) 420a. In some embodiments, the 3D-tracked, screw-locking device (disengaged) 402a comprises an arm 410 that can pivot about the shaft 404, which can be locked in-place via a set screw (disengaged) 412a, and contains an attached DRF 408a that comprises a plurality of trackable markers 406.

Figure 4D:
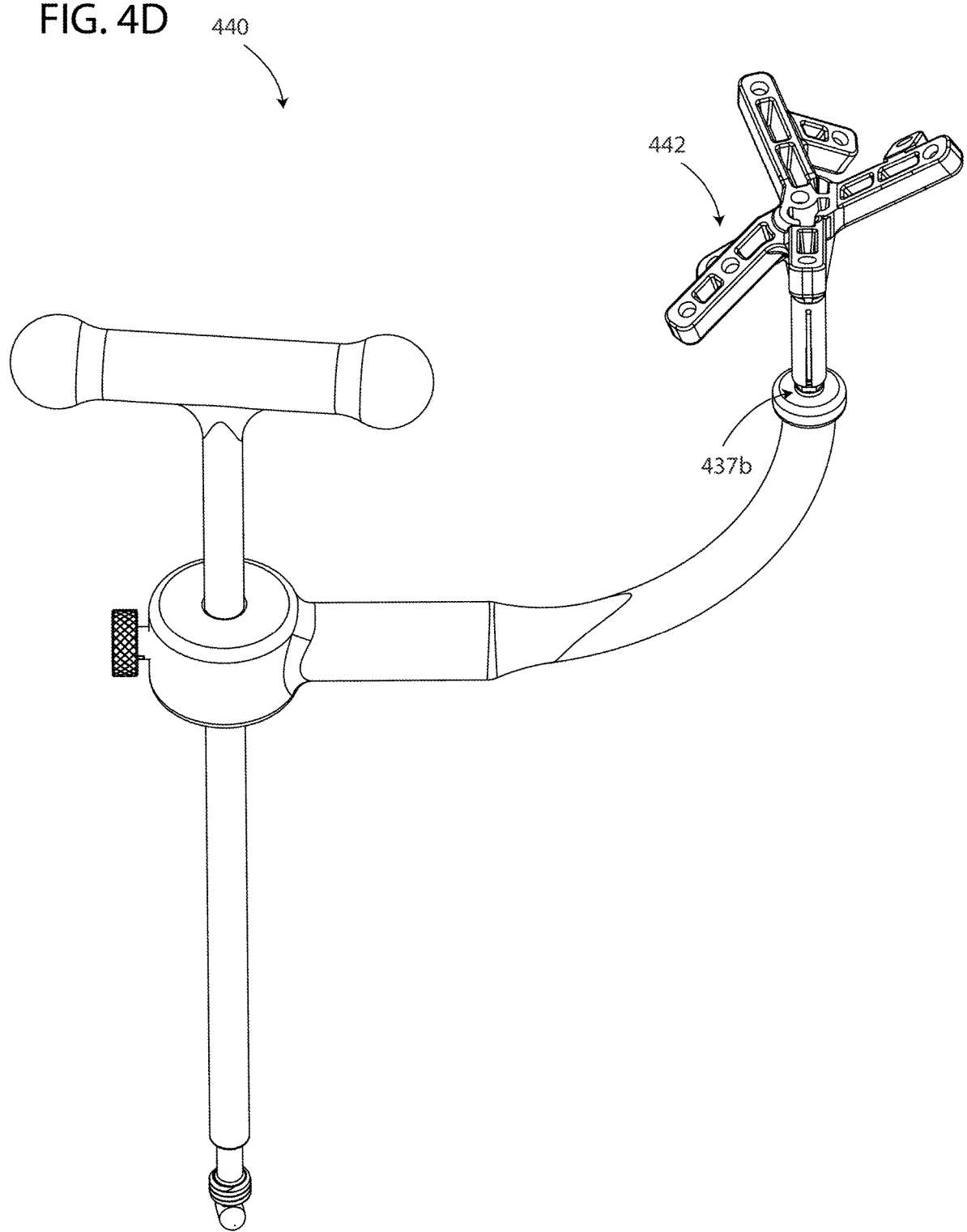
FIG. 4D illustrates a perspective view of an alternate design to enable XRay initialization of anatomical landmarks of interest for MIS procedures as described previously in relation to FIGS. 4A-C in accordance with some embodiments of the invention.

In some embodiments, FIG. 4B 430 and FIG. 4C 435 illustrate assembly views of alternate designs of the 3D-tracked, screw-locking device that enable alternate tracking methods for the device. In some embodiments, the device arm 432 can include an embedded fiducial marker device 437a similar to that shown previously in relation to FIGS. 1-3. In some embodiments, FIG. 4D illustrates an assembly view 440 in which the screw-locking device can be tracked in real-time via a DRF, tracked intermittently via a fiducial-based registration with a 3D-tracked probe or tracked end effector, or tracked intermittently with non-navigation initialization (e.g., initialized via X-Ray adapter device). In some embodiments, the tracking device can be initialized relative to attached vertebra and/or implants of interest (not shown) via an X-Ray initialization adapter device (442) mated onto a fiducial registration device (engaged, initialized) 437b.

In some embodiments, FIG. 4E 450 and FIG. 4F 460 illustrate assemblies of the 3D-tracked, screw-locking device that engages with a minimally-invasive-designed polyaxial screw that includes a percutaneous extension sleeve. In some embodiments, the screw-locking device (engaged) 402b is engaged coaxially with the MIS screw (locked, tracking) 452b via the compression of the screw's compressible tab 458, which substantially locks the screw in a 3D orientation. In some embodiments, the tab 458 is compressed via the locking device's set screw 418 which engages screw threads (not shown) in the wall of the MIS screw 452b and compresses a rod-like interface (engaged) 420b against the tab 458. In some embodiments, when the MIS screw (locked, tracking) 452b is substantially locked, the angle between its screw thread shaft 456 and the upper tulip's walls cannot be adjusted until the screw-locking device (engaged) 402b is fully disengaged. In some embodiments, the set screw 418 and the related interface features are engaged via the actuation of the locking device's handle 414.

Figure 4G:
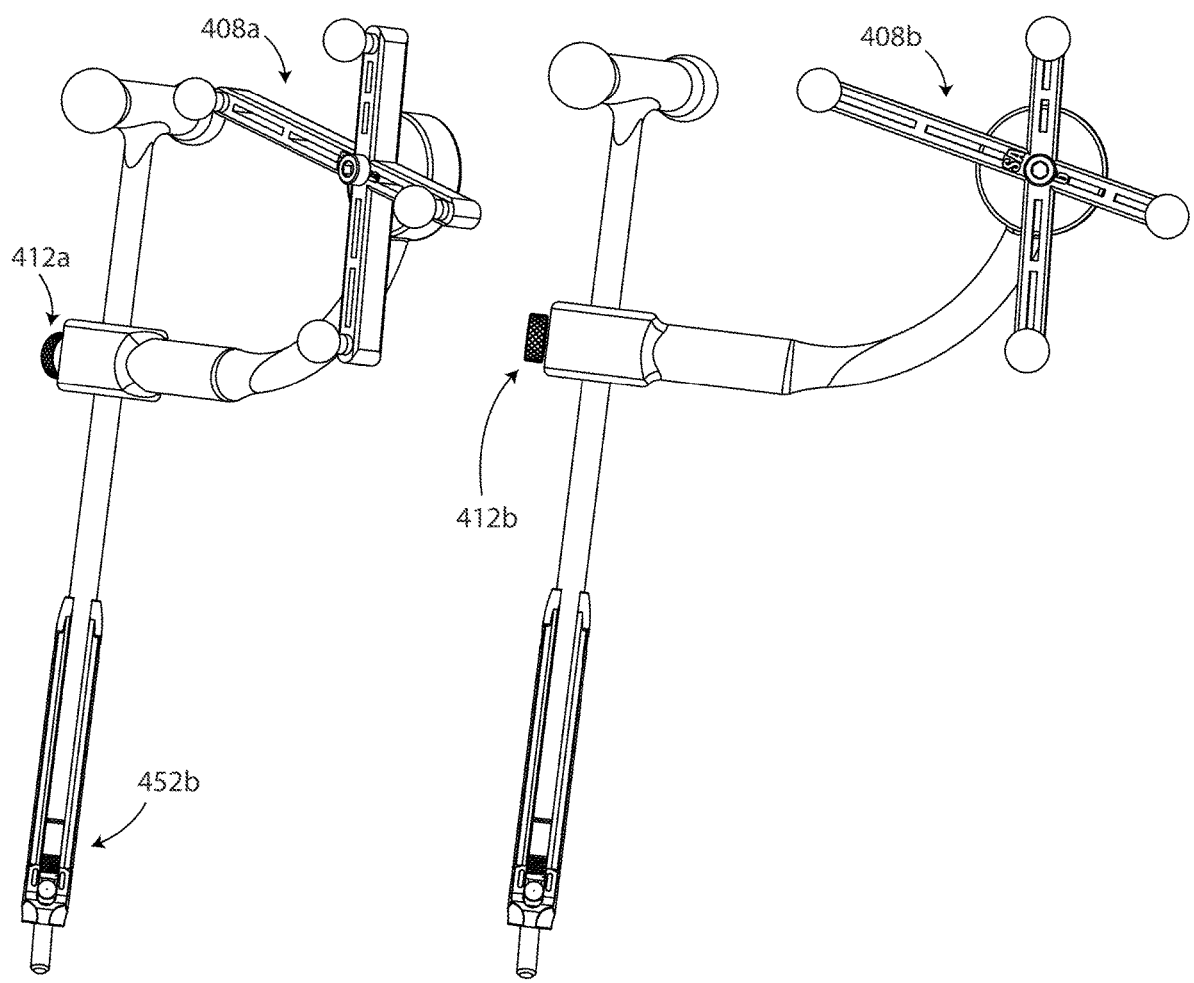
FIG. 4G illustrates perspective views of the tracking device array being adjusted for tracking visualization while the device is engaged to the MIS percutaneous screws as described previously in relation to FIGS. 4A-F in accordance with some embodiments of the invention.

In some embodiments, FIG. 4G illustrates an assembly view 470 in which a 3D-tracked, screw-locking device that is substantially engaged with an MIS screw can have its DRF face pose adjusted (e.g., both height and angle) relative to the device shaft in order to enable for reliable visualization and line of sight by a tracking system (e.g., NDI Polaris Spectra camera). In some embodiments, the 3D-tracked, screw-locking device's tracking arm can rotate about the device shaft and become substantially locked in-place via a set screw (engaged) 412b.

Figure 4H:
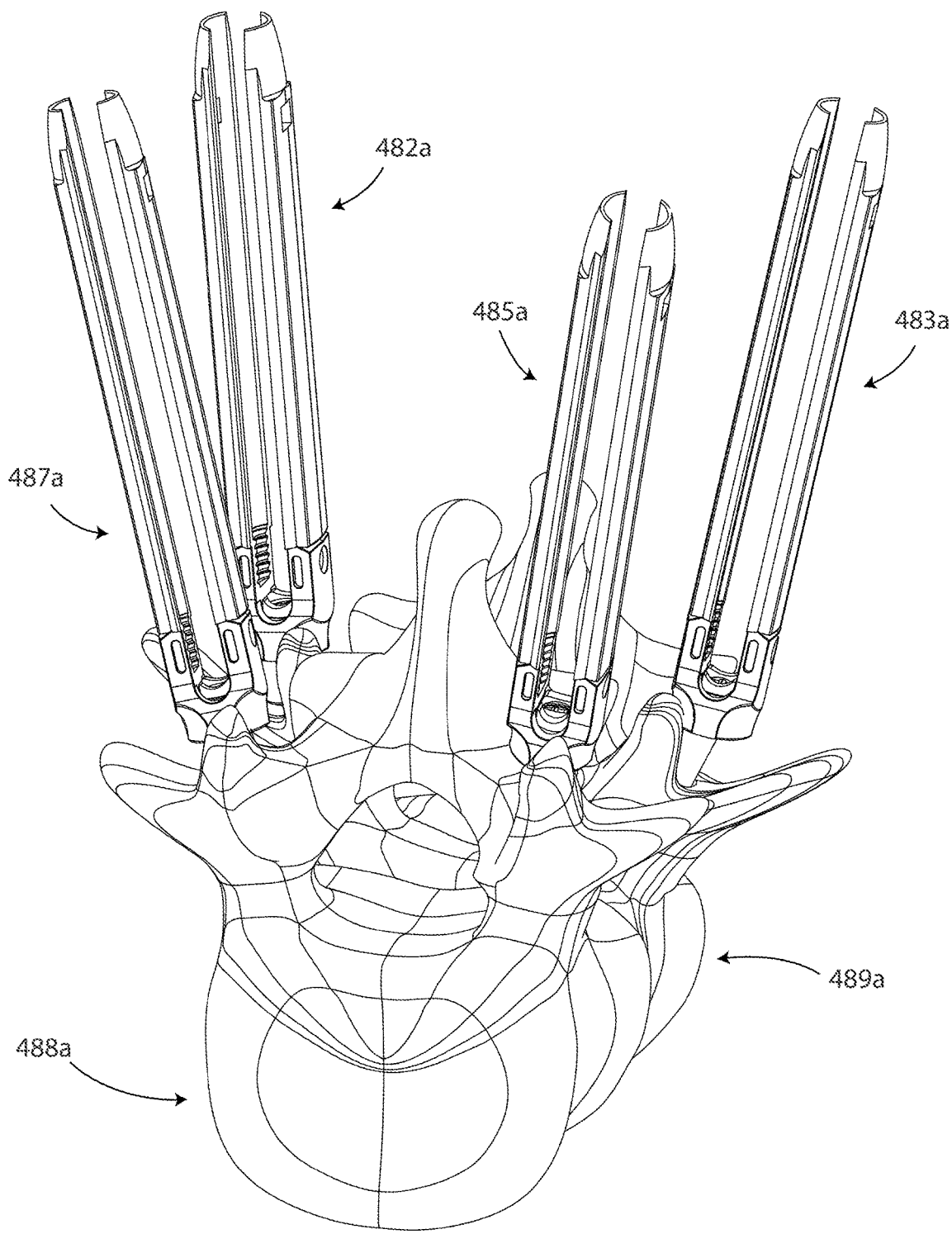
FIG. 4H illustrates a perspective view of two vertebrae with MIS percutaneous screw towers attached as described previously in relation to FIGS. 4A-G in accordance with some embodiments of the invention.
Figure 4I:
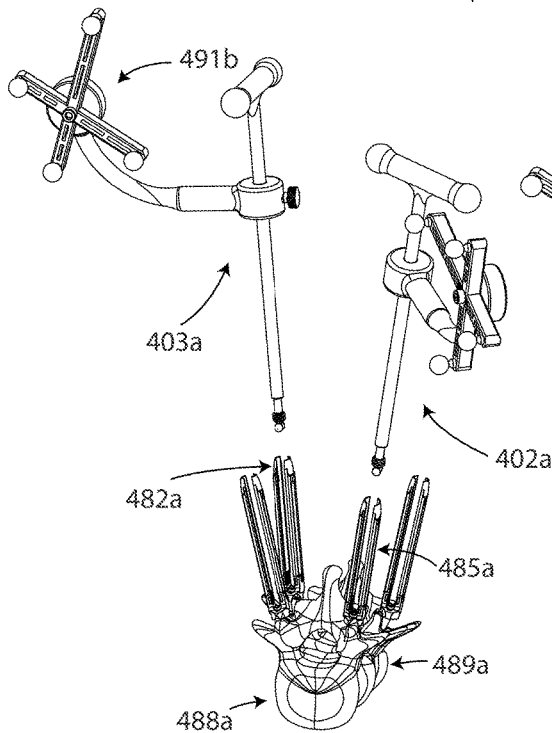
FIGS. 4I-L illustrates the process of engaging the tracking devices to the MIS percutaneous screw towers and enabling tracking of individual vertebrae as described previously in relation to FIGS. 4A-H in accordance with some embodiments of the invention.
Figure 4J:
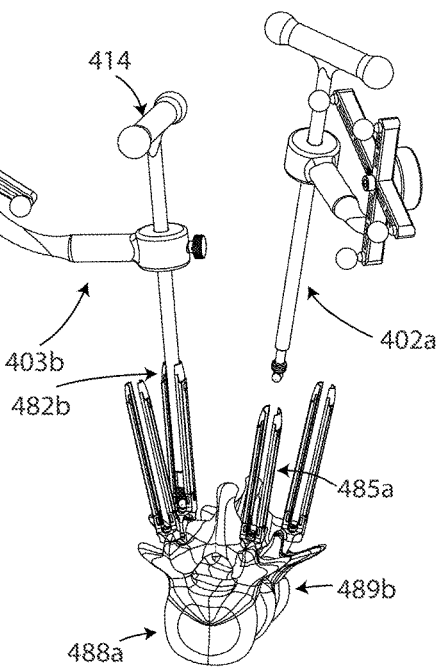
Figure 4K:
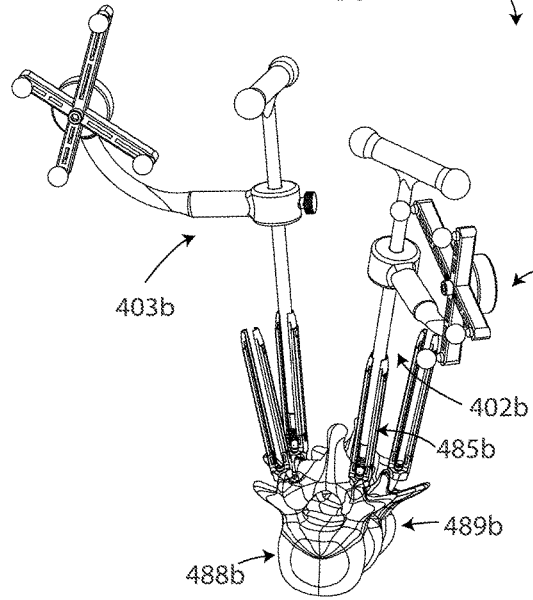
Figure 4L:
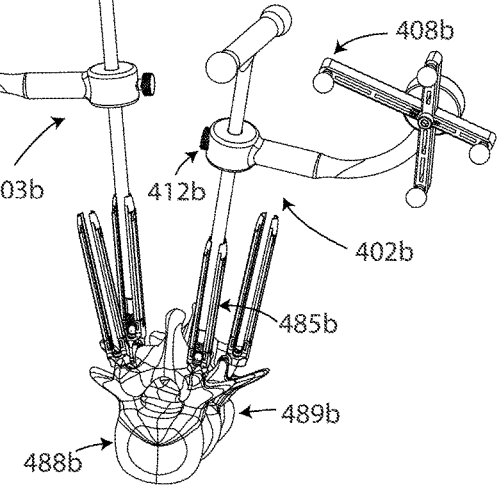

In some embodiments, FIG. 4H illustrates an assembly view 480 of a plurality of vertebrae of interest with implanted MIS screws. In some embodiments, the superior vertebra (not tracked) 488a and the inferior vertebra (not tracked) 489a each contain two MIS screws. In some embodiments, the vertebrae can be manipulated from a surgical approach that is not a posterior fusion (e.g., lateral, XLIF, OLIF, TLIF).

In some embodiments, FIG. 4I 490, FIG. 4J 492, FIG. 4K 493, and FIG. 4L 494 illustrate assembly views of the vertebrae of interest with MIS screws and the process of engaging the 3D-tracked, screw-locking devices to the vertebrae to enable real-time tracking of the vertebrae. In some embodiments, the vertebrae are registered via state-of-the-art image-guided navigation (e.g., fusion to preop or intraop CT/MRI imaging or intraop X-Ray images) and then segmented with a unique identity and 3D meshwork, which may include labeled landmarks of interest (e.g., endplate, vertebral body centroid, etc.), that can be assigned and tracked by each respectively engaged screw-locking device. In some embodiments, a superior screw-locking device (engaged) 402b is engaged and fully locking one or more MIS screws (locked, tracking) 485b on the superior vertebra. In some embodiments, one or more 3D-tracked, screw-locking devices can be engaged to a vertebra and one or more 3D-tracked, screw-locking devices can be used in total to track the 3D location and orientation of engaged, adjacent, or mechanically-coupled landmarks of interest (e.g., adjacent vertebrae). In some embodiments, an inferior 3D-tracked, screw-locking device (engaged) 403b is substantially engaged and locking an MIS screw (locked, tracking) 482b that is embedded in the inferior vertebra of interest. In some embodiments, once the MIS screws are substantially locked via the engaged tracking devices, the movement of the MIS screws or their respective extensions enable direct manipulation of the attached vertebrae of interest, thus enabling for tracking of the motion of the vertebra and relevant landmarks of interest via tracking of the locked MIS screws.

Figure 4M:
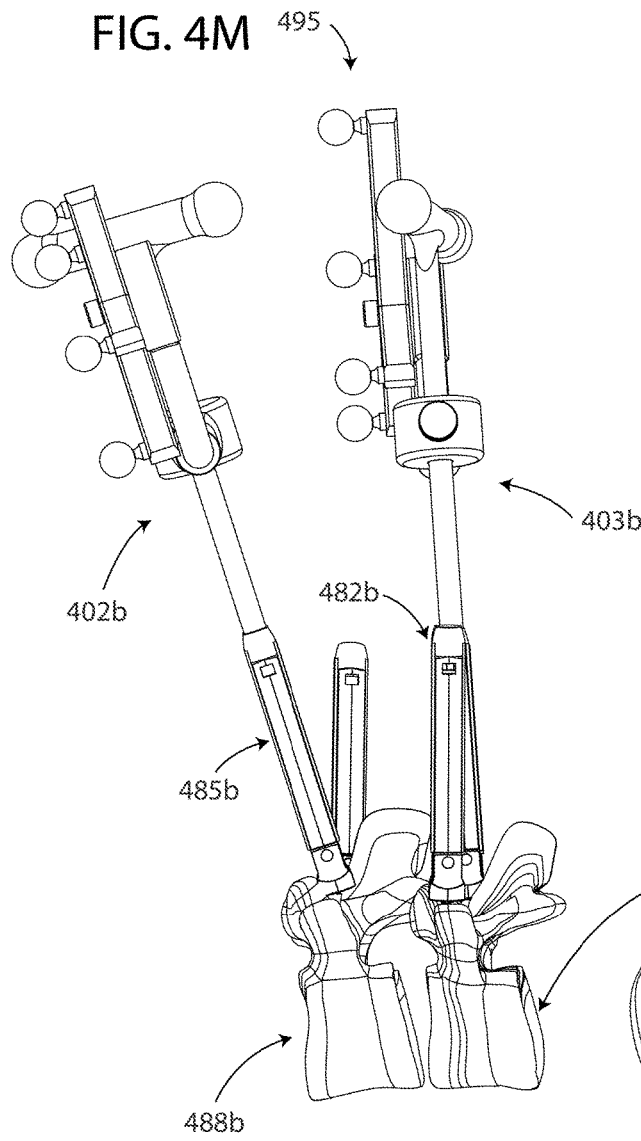
FIG. 4M illustrates a side view of the tracking device attached to the MIS percutaneous screw towers in the vertebrae as described previously in relation to FIGS. 4A-L in accordance with some embodiments of the invention.
Figure 4N:
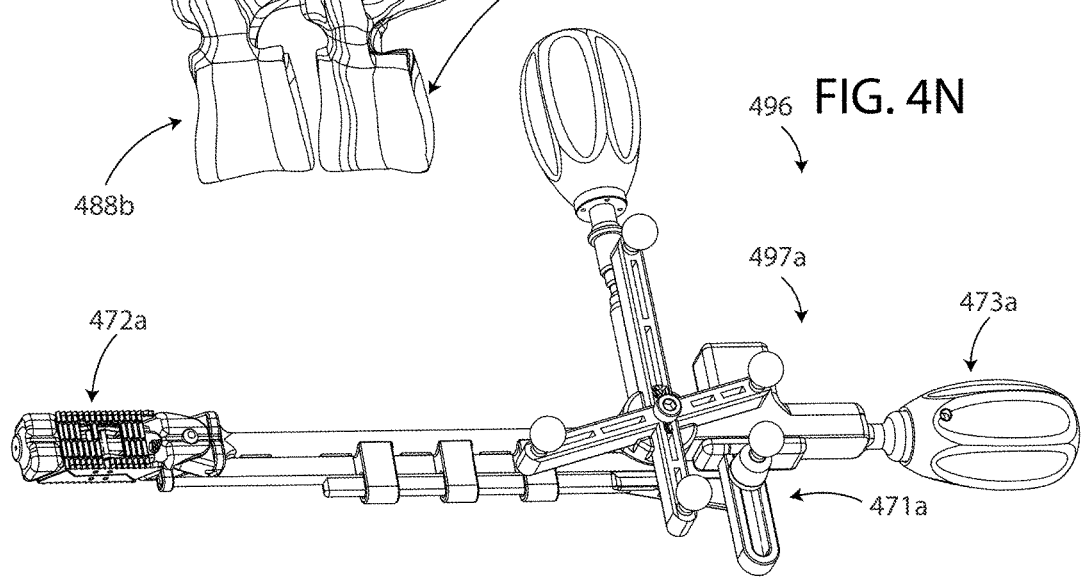
FIG. 4N illustrates a side view of a 3D-tracked driver for insertion and manipulation of an interbody cage as described previously in relation to FIGS. 4A-M in accordance with some embodiments of the invention.

In some embodiments, FIG. 4M illustrates an assembly side view 495 of the vertebrae of interest and their engaged 3D-tracked, screw-locking devices. In some embodiments, a 3D-tracked implant driver (which is also described previously in relation to U.S. continuation-in-part application Ser. No. 16/926,390) can track the 3D location and orientation of an interbody cage, both during placement of the cage and deployment (e.g., expansion, pivoting). In some embodiments, FIG. 4N illustrates an assembly view 496 of a 3D-tracked implant driver (not inserted yet) 497a that comprises at least a shaft, DRF array, a TMSM (inactive) 471a with an included mechanism for tracking multi-directional motion of the cage (not implanted) 472a, and a handle (not rotated yet) 473a which controls the deployment of the cage 472a.

Figure 4O:
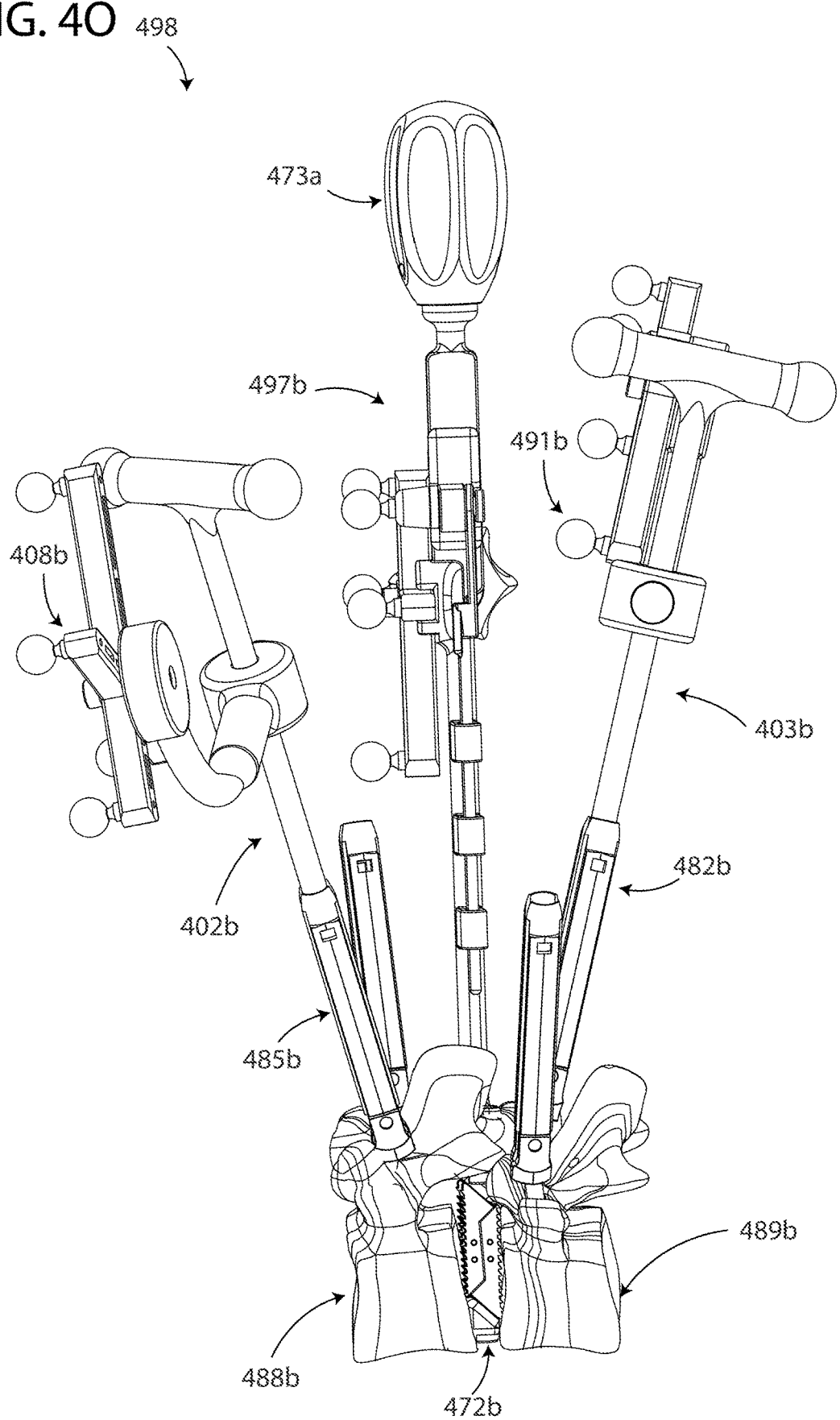
FIGS. 4O-P illustrates the process of combining the vertebrae-tracking device and the 3D-tracked driver to enable 3D-tracking of the location and orientation of vertebrae during interbody cage placement and manipulation, as described previously in relation to FIGS. 4A-N in accordance with some embodiments of the invention.
Figure 4P:
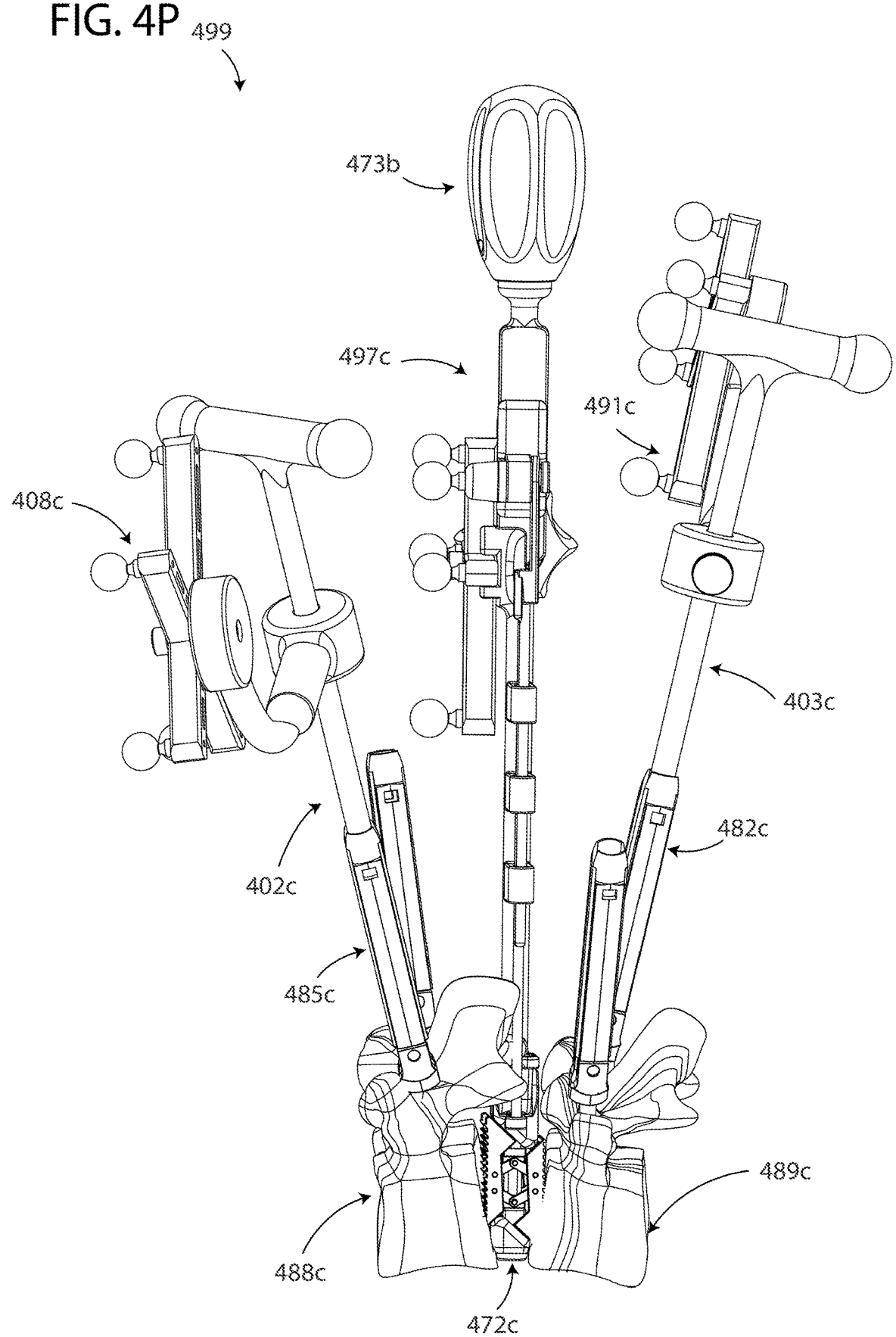

In some embodiments, FIG. 4O illustrates an assembly view 498 of a 3D-tracked implant driver (inserted) 497b that is wedged between the superior vertebra (engaged with cage) 488b and inferior vertebra 489b (engaged with cage) of interest. In some embodiments, FIG. 4P illustrates an assembly view 499 that involves a 3D-tracked implant driver (deployed cage) 497c that has fully actuated the attached interbody cage (expanded) 472c and thus adjusted the 3D position and orientation of the adjacent inferior vertebra (moved) 489*a* and superior vertebra (moved) 488*c*. In some embodiments, when the vertebrae are manipulated via the placement and/or actuation of the interbody device 472*c*, the attached inferior MIS screw (locked, moved) 482*c* and superior MIS screw (locked, moved) 485*c* move the engaged inferior screw-locking device (engaged, tracking, moved) 402*c* and inferior screw-locking device (engaged, tracking, moved) 403*c* via the same rigid body transform that the manipulated vertebrae have experienced.

In some embodiments, the system utilizes this calculated amount of cage expansion to provide the user with real-time, 3D visualization of the cage expanding while it is implanted into the spine. Some embodiments of the invention involve tracking vertebrae in real-time, using DRF attachments on bone-mounted fiducials, during the insertion of implants via a 3D-tracked implant driver. In some embodiments, when the user desires real-time tracking of engaged vertebrae, a 3D-tracked DRF attachment can mate with bone-mounted fiducials on each vertebra and provide feedback on the vertebra's 3D location and pose while the system also provides feedback on the real-time location and actuation configuration of an implant engaged to a 3D-tracked driver. In some embodiments, the engaged vertebrae of interest are initialized relative to their attached, bone-mounted fiducial via image-registration processes. In some embodiments, these anatomy initialization processes include compatibility for both image-guided navigation (e.g., CT-guidance and automated segmentation of 3D vertebrae) and X-Ray imaging surgical workflows.

Some embodiments of the system involve handling different calibration requirements for different X-Ray imaging systems (e.g., 3D imaging, 2D imaging with flat-panel detector, image intensifier, etc.). In some embodiments, imaging systems, such as an image intensifier, require correcting for image distortions. In some embodiments, this is accomplished by attaching an image distortion correction device to the imaging system (e.g. to the detector). In some embodiments, the radiopaque markers (e.g., spheres, lines, grid, disks, etc.) of the image distortion correction device are then segmented and analyzed in X-Ray images to compute distortion correction parameters. In some embodiments, the distortion correction parameters are used to correct each X-Ray image. In some embodiments, the surgeon may track the X-Ray imaging system to perform the 3D registration of anatomical landmarks. In some embodiments, a 3D-tracked dynamic reference frame (DRF) is attached to the X-Ray imaging system, and the locations of the X-Ray source and the principal point are estimated (e.g. by tapping the centers of the detector and emitter with a 3D-tracked probe). In some embodiments, X-Ray images of the bone-mounted fiducial are then acquired from two or more different views ensuring that both the X-Ray adapter device and the anatomical landmarks of interest are visualized. In some embodiments, for each acquired image, the 3D location and pose of the DRF on the X-Ray imaging system is recorded. In some embodiments, the surgeon does not track the X-Ray imaging system and simply proceeds with the image acquisitions from two or more views of the bone-mounted fiducial and X-Ray adapter device.

In some embodiments, the system calibrates the projective geometry of the acquired X-Ray images, identifying an appropriate projection mapping from 3D-space to the 2D-image plane. Some embodiments of this process include using numerical optimization (e.g., minimizing the reprojection error of the X-Ray adapter's radiopaque markers), while some embodiments utilize algorithms such as the Direct Linear Transform (DLT) and its variants. In some embodiments, the system employs different geometric models (e.g., 6-DOF, 7-DOF, 9-DOF solutions) depending on the X-Ray imaging system and the desired calibration process (e.g., tracking the X-Ray imaging system, using bone-mounted fiducials, using offline calibrations provided by manufacturer or technician, etc.). Some embodiments of the invention calibrate the geometry based on the tracked X-Ray imaging system, using the location and pose of the 3D-tracked DRF in each image.

In some embodiments, bony anatomical landmarks of interest (e.g., S1 endplate, femoral head, etc.) are segmented in each X-Ray image. Some embodiments involve using automated computer vision algorithms to detect the edges and boundaries of the landmarks of interest, while some embodiments rely on the user to manually annotate the landmarks using points, lines, polygons, or region inputs.

In some embodiments, the landmarks are then triangulated in 3D space with respect to the X-Ray adapter device's coordinate frame. In some embodiments, the landmark of interest is a "point" landmark (e.g., femoral head centroid) triangulated via numerical optimization (e.g., minimizing the reprojection error) or analytically (e.g., least-squares, Perspective-n-Point) from point, line, or region segmentations in the image. In some embodiments, the landmark of interest is a "plane" landmark (e.g., S1 endplate), triangulated from line or region segmentations in the image. In some embodiments, the landmark of interest is a "volume" landmark (e.g., L5 vertebra, pelvis, etc.), triangulated from region segmentations in the image.

In some embodiments, if a 3D imaging system is used (e.g., CT, CBCT, etc.), the step of determining the locations of anatomical landmarks relative to the X-Ray adapter device is accomplished by simply segmenting them in the 3D volume.

In some embodiments, any landmarks that were not segmented in X-Ray images may be localized based on known anatomical measurements of the patient (e.g., pre-operative planning alignment parameters, such as pelvic incidence and bicoxofemoral axis distance, or 3D imaging inputs, etc.) in relation to landmarks that are already triangulated, or based on normative patient data. In some embodiments, this process will typically be used if an anatomical landmark of interest is challenging to visualize in X-Ray images.

In some embodiments, once the anatomical landmarks have been triangulated relative to the X-Ray adapter device, the fiducial-to-landmark 3D registration process is complete, and the X-Ray adapter device is removed from the bone-mounted fiducial. In some embodiments, the aforementioned processes may be repeated to register additional bony landmarks of interest.

Some embodiments of this invention enable the user to update the location of anatomical landmarks at any time during surgery, without the need for additional X-Ray imaging. In some embodiments, the user mates a 3D-tracked probe to the bone-mounted fiducial and records the probe's location and pose in the navigation camera's coordinate frame. In some embodiments, based on the probe's location and pose and the identical probe-to-fiducial and fiducial-to-adapter mating mechanisms, the system computes the virtual positions of the X-Ray adapter markers. In some embodiments, using the virtual positions of the X-Ray adapter markers, the system computes the rigid body transform between the X-Ray adapter's coordinate frame and the navigation camera's coordinate frame. In some embodiments, this rigid body transform is applied to the registered anatomical landmarks, which computes the new 3D coordinates of the anatomical landmarks in the navigation camera's coordinate frame. In some embodiments, the locations of the anatomical landmarks and non-fiducial-based inputs (e.g., bilateral laminae tracings) can be transformed to align with the patient's anatomical planes using one of the anatomical landmarks to define the origin and axes (e.g., S1 endplate defines patient left, right, posterior, anterior, superior, inferior). In some embodiments, the user holds the probe parallel with the patient's body and triggers the probe to record its location and pose, and the system sets that as the coordinate frame for subsequent measurements.

In some embodiments, the updated 3D locations of the anatomical landmarks, along with any available non-fiducial-based inputs, are used to compute the spinal alignment parameters of the patient. In some embodiments, if non-fiducial-based inputs are not available, the anatomical landmarks themselves may be used to compute desired spinal alignment parameters.

In some embodiments, the process of updating the 3D locations of the anatomical landmarks and computing new spinal alignment parameters may be repeated any number of times during surgery without taking additional X-Ray images.

Some embodiments of the invention involve implanting fiducials into multiple bony anatomical landmarks of interest (e.g., pelvis and multiple lumbar vertebrae) for geometric calibration and 3D registration. In some embodiments, for a group of bone-mounted fiducials that can all be visualized in an X-Ray image, just one of them is attached to an X-Ray adapter device with embedded radiopaque markers (e.g., spheres, lines, grid, disks, etc.) via a unique mating mechanism.

In some embodiments, depending on the type of X-Ray imaging system used (e.g., image-intensifier), image distortion correction processes as described previously in relation to FIG. 157 are performed. In some embodiments, this image-distortion-correction step is not required (e.g. 2D imaging with flat-panel detector), and the surgeon simply proceeds with acquiring at least two X-Ray images of the bone-mounted fiducials and the X-Ray adapter device.

In some embodiments, the system calibrates the projective geometry of the acquired X-Ray images, identifying an appropriate projection mapping from 3D-space to the 2D-image plane. In some embodiments, this process is performed in accordance with processes described previously in relation to FIG. 157.

In some embodiments (e.g., 3D imaging), the anatomical landmark triangulation processes described above are circumvented, by simply segmenting the anatomical landmarks within the provided 3D volume, to compute the 3D locations of the landmarks relative to the X-Ray adapter device.

Some embodiments of this invention enable the user to update the location of anatomical landmarks at any time during surgery, without the need for additional X-Ray imaging. In some embodiments, the user engages a 3D-tracked probe to the bone-mounted fiducials in a software-guided order. In some embodiments, this process defines the unique vertebral-level identities of the bone-mounted fiducials (e.g., fiducial #1 is mounted to the L3 vertebra) and records their 3D locations and poses in the navigation camera's coordinate frame.

In some embodiments, for each vertebral level (e.g., L3 vertebra), the system computes the 3D location of its corresponding anatomical landmark (e.g., endplate of L3 vertebra) in its unique fiducial's coordinate frame (e.g., fiducial mounted to the L3 vertebra). In some embodiments, this process is performed by using the defined vertebra-fiducial pairing and a rigid body transform applied to the registered anatomical landmarks in the navigation camera's coordinate frame. In some embodiments, the system is now ready to compute spinal alignment parameters of the patient. In some embodiments, the user may repeat the 3D registration process for other anatomical landmarks of interest before proceeding.

In some embodiments of this invention, the 3D locations and poses of anatomical landmarks are used to compute the spinal alignment parameters of the patient. In some embodiments, if the anatomy has been manipulated or accidentally moved during the surgical correction process, new spinal alignment parameters can be measured by engaging the 3D-tracked probe with each of the bone-mounted fiducials in the same software-guided order as prior and updating the 3D locations and poses of anatomical landmarks.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, some embodiments include methods can be processed by one or more machines or processors that can be coupled over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous some embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A system for registering at least a portion of a patient's spinal curvature and/or flexibility, comprising:
    an acquisition system for acquiring data using a continuous or discrete 3D-tracked acquisition along a surface of a spine of the patient;
    non-transient computer readable media for storing at least a portion of the acquired data;
    one or more computer processors configured to analyze at least a portion of the acquired data and generating a quantitative assessment of the patient's spinal biomechanical qualities,
    wherein the acquisition system includes a fiducial marker device with a registration interface and bone fixation features, wherein the registration interface includes a tapered cylindrical protrusion with a back surface and a keyed front surface used for mating with a 3-D tracked probe, wherein the registration interface is configured to be received inside a tip of the 3-D tracked probe during registration,
    wherein the 3-D tracked probe registers continuous points along a surface of the spine of the patient,
    wherein the 3-D tracked probe includes a depressible trigger button to enable an active state for registering points on the surface of the spine.

2. The system of claim 1,
    wherein the system provides location-based input regarding one or more implants used to enhance the biomechanical qualities.

3. The system of claim 1,
    wherein the system acquires data both within and beyond a proposed surgical site.

4. The system of claim 1,
    wherein the system registers at least one instrument or implant used to assess and/or manipulate the conformation of the spine.

5. The system of claim 1,
    wherein the quantitative assessments include calculated values for one or more radiographic parameters related to both global and segmental alignment of the spine.

6. The system of claim 1,
    wherein the one or more radiographic parameters include at least one of lumbar lordosis, central sacral vertical line, T1 pelvic angle, thoracic kyphosis, and Cobb angle.

7. The system of claim 1, wherein the one or more processors implement filtering to aid in identifying a relationship between acquired points and anatomical regions of interest.

8. The system of claim 1,
    wherein the quantitative assessment includes values for Cobb angle, lumbar lordosis, thoracic kyphosis, C2-C7 lordosis, C7-S1 sagittal vertical axis, central sacral vertical line, T1 pelvic angle, pelvic incidence, and pelvic-incidence-lumbar-lordosis mismatch.

9. The system of claim 1,
    further including a visual display and quantitative feedback system for assessing and adjusting implants that can be implanted into or onto the patient.

10. The system of claim 9, wherein the display outputs at least one of information about the patient's spine's curvature and alignment, quantitative radiographic alignment parameter values, instrumented hardware analysis, flexibility or range of motion of the spine, and one or more ways to acquire or analyze radiographic images.

11. The system of claim 1, wherein the bone fixation features are self-tapping threads including a self-cutting flute.

* * * * *